(12) United States Patent
Smith-Espinoza et al.

(10) Patent No.: US 7,659,449 B2
(45) Date of Patent: Feb. 9, 2010

(54) REGULATION OF GENE EXPRESSION IN PLANTS

(75) Inventors: Claudia Jeanette Smith-Espinoza, Bonn (DE); Sathish Puthigae, Auckland (NZ); Jonathan Robert Phillips, Bonn (DE); Catherine Jane Bryant, Auckland (NZ); Kieran Michael Elborough, Franklin (NZ); Colin Robert South, Lexington, MA (US)

(73) Assignee: Fonterra Co-Operative Group Limited, Auckland (NZ)

( * ) Notice: Subject to any disclaimer, the term of this patent is extended or adjusted under 35 U.S.C. 154(b) by 87 days.

(21) Appl. No.: 11/501,283

(22) Filed: Aug. 8, 2006

(65) Prior Publication Data

US 2007/0089203 A1 Apr. 19, 2007

(30) Foreign Application Priority Data

Aug. 9, 2005 (NZ) .................................. 541710

(51) Int. Cl.
*A01H 5/00* (2006.01)
*C12N 15/82* (2006.01)
*C12N 15/87* (2006.01)
*C12N 5/14* (2006.01)
*C12N 15/63* (2006.01)
*C07H 21/04* (2006.01)
*C07H 21/00* (2006.01)

(52) U.S. Cl. ............... 800/295; 800/278; 800/289; 435/320.1; 435/419; 435/468; 536/23.1; 536/23.6; 536/24.1

(58) Field of Classification Search ............... None
See application file for complete search history.

(56) References Cited

U.S. PATENT DOCUMENTS 6,670,528 B1 * 12/2003 Shinozaki et al. ........... 800/298
2003/0221224 A1 * 11/2003 Zinselmeier et al. ........ 800/289

OTHER PUBLICATIONS

Wells (Biochemistry 29:8509-8517, 1990).*
Ngo et al., (The Protein Folding Problem and Tertiary Structure Prediction, K. Merz., and S. Le Grand (eds.) pp. 492-495, 1994).*
Keskin et al. (Protein Science, 13:1043-1055, 2004).*
Thornton et al. (Nature structural Biology, structural genomics supplement, Nov. 2000).*
Kim et al. (Plant Molecular Biology, 24:105-117, 1994).*
Donald et al. (EMBO J. 9:1717-1726, 1990).*
Benfey et al. (Science 250:959-966, 1990).*
Guo et al. (PNAS, 101: 9205-9210, 2004).*
Keil et al. (The EMBO Journal, 8:1323-1330, 1989).*
Cellier et al., "Molecular and physiological responses to water deficit in drought-tolerant and drought-sensitive lines of sunflower," Plant Physiol., 1998, vol. 116, pp. 319-328.
Gaxiola et al., "Drought- and salt-tolerant plants result from overexpression of the AVP1 $H^+$ -pump," PNAS, Sep. 25, 2001, vol. 98, No. 20, pp. 11444-11449.
Kasuga et al., "Improving plant drought, salt, and freezing tolerance by gene transfer of single stress-inducible transcription factor," Nature Biotechnology, Mar. 1999, vol. 17, pp. 287-291.
Kim et al., "Isolation and characterization of cDNAs encoding the vacuolar $H^+$ -pyrophosphatase of *Beta vulgaris*," Plant Physiol., 1994, vol. 106, pp. 375-382.
Natali et al., "Light induces expression of a dehydrin-encoding gene during seedling de-etiolation in sunflower (*Helianthus annuus* L.)," Journal of Plant Physiology, 2007, vol. 164, pp. 263-273.
Robertson, Masumi, "Increased dehydrin promoter activity caused by HvSPY is independent of the ABA response pathway," The Plant Journal, 2003, vol. 34, pp. 39-46.
Robertson et al., "Sequence analysis and hormonal regulation of a dehydrin promoter from barley, *Hordeum vulgare*," Physiologia Plantarum, 1995, vol. 94, pp. 470-478.

* cited by examiner

*Primary Examiner*—Vinod Kumar
(74) *Attorney, Agent, or Firm*—Knobbe Martens Olson & Bear LLP

(57) ABSTRACT

Isolated stress-responsiveness promoters suitable for directing gene expression in plant cells or plants are provided, along with constructs, vectors, host cells, plant cells and plant comprising the promoters. Methods for producing plant cells or plants with modified phenotype via transformation of the plant cells or plants with the promoters are also provided.

19 Claims, 5 Drawing Sheets

Figure 1

```
GGCTGGTAAA  ACAAATATAA  GTATTAATAT  AAATATAATA  CAATAGAAGG   -1126
AAAATAAATA  AAATTTCCCT  CTGTGCCGTG  CAAAAATGCA  CGGCAATGGG   -1076
CTGGCCCGCA  CGGCAAAGGC  ATCGTTGCCG  TGTCCACGGC  AATGGGTTGG   -1026
CCCGCACGGC  AAAGGCATCG  TTGCCGTGTC  CACGTCTTCG  CCGTGCGCCT   -976
TGGCTCTATC  TTTGCCGTGA  AGCGTTCTTT  GCCGTGTGCC  TTTTATTTCT   -926
TTGCCGTGGG  ATGCTGCCTT  TGCCGAGCGC  TGAGCTGGCG  CTTTGCCGTG   -876
CGCGTATTGT  TTGCCGTGCG  TCGTCCCAGA  GCTGTACGGC  AAAGAATTCA   -826
CTGCCGTGCA  CGAGACACAC  GGGAAAGAAG  TTTTGCATGG  CAAAGGGCGC   -776
TGACAGCACA  CGGCAAAGAG  CCTGGCACGG  CATTGAGCTT  TTTTCCCGTA   -726
ATGATAGACG  GCATAATATA  ATGGACGCAC  ATGCTGATGT  CAGGATGTCA   -676
CCCACTCATC  CTAGTATTTG  TGG__GACGTG__A  ATTCTTTGTG  AGATGGGCAA   -626
TGGGGTGTGA  ACAAAATAAG  TTTTGTACTA  GTAGATAAAC  ATTTTTACCC   -576
ATAAACAATT  GTTCTGTATT  GAATGAGAAA  TTATTTTGTA  CTGGATGAAA   -526
ATTTTCTGAG  TAACTGTGTA  AGATTAACAT  NAATCAAGAG  ACAAATCCAA   -476
TGGCTACAAA  GTCAACTAAT  ACTTGTTAAA  AGTTCCGATA  CTTAAAATTA   -426
TCAAAACTGA  TATATAGAAT  ATTGCCCATC  TCGCCACCGT  GCTAGTTTAA   -376
CAGACGATGG  ACGAATATCA  GTCTTGTATT  GGATAATCGA  TGCATGCGAG   -326
CTATCGGC__CA__  __CCT__GTCCATG  CTTCCAGAAG  GAGCCGA__GAC__  __GTG__GCGACTT   -276
CGTCCGACGC  GCCGACTATC  TGCACACGCC  CGGCTTCTCG  TCGTGGGCGA   -226
GTCAGCAGTT  ACGGGCTTTC  CGCCTACCAA  CTCACACGTA  GCGCCCTATC   -176
GTGGCGCTTG  ATCGATGCAA  CAGCGATGCC  TATCCAGCT  CCTCAAGCTG   -126
CT__TATA__AGTA  TGTCCTCGGC  CATCACTGCT  TACACAACAA  ACACAGCTAC   -76
TTATCGCAGT  GTACTAAACA  AGACGTACTA  GCTAGATTTC  GTGAGGTAAA   -26
ATCAGTGCAA  TATCACTTGT  GCAAG__ATG__                           +3
```

| Name | Start | End | |
|---|---|---|---|
| RB | 261 | 286 | |
| KanR | 5313 | 6095 | |
| LB | 6520 | 6545 | |
| 35S 3'Term | 6810 | 6595 | C |
| Hpt | 7861 | 6839 | C |
| 35S Prom | 8678 | 7897 | C |
| dhn promoter | 8944 | 10118 | |
| VP gene | 10127 | 14696 | |
| VP 3' UTR' | 14697 | 15888 | |

SEQUENCE LISTING

<160> NUMBER OF SEQ ID NOS: 31

<210> SEQ ID NO 1
<211> LENGTH: 1175
<212> TYPE: DNA
<213> ORGANISM: Lolium perenne
<220> FEATURE:
<221> NAME/KEY: misc_feature
<222> LOCATION: (681)...(681)
<223> OTHER INFORMATION: n = a, t, c, or g

<400> SEQUENCE: 1

```
ggctggtaaa acaaatataa gtattaatat aaatataata caatagaagg aaaataaata      60
aaatttccct ctgtgccgtg caaaaatgca cggcaatggg ctggcccgca cggcaaaggc     120
atcgttgccg tgtccacggc aatgggttgg cccgcacggc aaaggcatcg ttgccgtgtc     180
cacgtcttcg ccgtgcgcct tggctctatc tttgccgtga agcgttcttt gccgtgtgcc     240
ttttatttct ttgccgtggg atgctgcctt tgccgagcgc tgagctggcg ctttgccgtg     300
cgcgtattgt ttgccgtgcg tcgtcccaga gctgtacggc aaagaattca ctgccgtgca     360
cgagacacac gggaaagaag ttttgcatgg caaagggcgc tgacagcaca cggcaaagag     420
cctggcacgg cattgagctt ttttcccgta atgatagacg gcataatata atggacgcac     480
atgctgatgt caggatgtca cccactcatc ctagtatttg tgggacgtga attctttgtg     540
agatgggcaa tggggtgtga acaaaataag ttttgtacta gtagataaac atttttaccc     600
ataaacaatt gttctgtatt gaatgagaaa ttattttgta ctggatgaaa attttctgag     660
taactgtgta agattaacat naatcaagag acaaatccaa tggctacaaa gtcaactaat     720
acttgttaaa agttccgata cttaaaatta tcaaaactga tatatagaat attgcccatc     780
tcgccaccgt gctagtttaa cagacgatgg acgaatatca gtcttgtatt ggataatcga     840
tgcatgcgag ctatcggcca cctgtccatg cttccagaag gagccgagac gtggcgactt     900
cgtccgacgc gccgactatc tgcacacgcc cggcttctcg tcgtgggcga gtcagcagtt     960
acgggctttc cgcctaccaa ctcacacgta gcgccctatc gtggcgcttg atcgatgcaa    1020
cagcgatgcc tatcccagct cctcaagctg cttataagta tgtcctcggc catcactgct    1080
tacacaacaa acacagctac ttatcgcagt gtactaaaca agacgtacta gctagatttc    1140
gtgaggtaaa atcagtgcaa tatcacttgt gcaag                              1175
```

<210> SEQ ID NO 2
<211> LENGTH: 1089
<212> TYPE: DNA
<213> ORGANISM: Lolium perenne
<220> FEATURE:
<221> NAME/KEY: misc_feature
<222> LOCATION: (611)...(611)
<223> OTHER INFORMATION: n = a, c, g, or t -continued

<400> SEQUENCE: 2

```
ctgtgccgtg caaaaatgca cggcaatggg ctggcccgca cggcaaaggc atcgttgccg      60
tgtccacggc aatgggttgg cccgcacggc aaaggcatcg ttgccgtgtc cacgtcttcg     120
ccgtgcgcct tggctctatc tttgccgtga agcgttcttt gccgtgtgcc ttttatttct     180
ttgccgtggg atgctgcctt tgccgagcgc tgagctggcg ctttgccgtg cgcgtattgt     240
ttgccgtgcg tcgtcccaga gctgtacggc aaagaattca ctgccgtgca cgagacacac     300
gggaaagaag ttttgcatgg caaagggcgc tgacagcaca cggcaaagag cctggcacgg     360
cattgagctt ttttcccgta atgatagacg gcataatata atggacgcac atgctgatgt     420
caggatgtca cccactcatc ctagtatttg tgggacgtga attctttgtg agatgggcaa     480
tggggtgtga acaaaataag ttttgtacta gtagataaac attttttaccc ataaacaatt    540
gttctgtatt gaatgagaaa ttattttgta ctggatgaaa attttctgag taactgtgta     600
agattaacat naatcaagag acaaatccaa tggctacaaa gtcaactaat acttgttaaa     660
agttccgata cttaaaatta tcaaaactga tatatagaat attgcccatc tcgccaccgt     720
gctagtttaa cagacgatgg acgaatatca gtcttgtatt ggataatcga tgcatgcgag     780
ctatcggcca cctgtccatg cttccagaag gagccgagac gtggcgactt cgtccgacgc     840
gccgactatc tgcacacgcc cggcttctcg tcgtgggcga gtcagcagtt acgggctttc     900
cgcctaccaa ctcacacgta gcgccctatc gtggcgcttg atcgatgcaa cagcgatgcc     960
tatcccagct cctcaagctg cttataagta tgtcctcggc catcactgct tacacaacaa    1020
acacagctac ttatcgcagt gtactaaaca agacgtacta gctagatttc gtgaggtaaa    1080
atcagtgca                                                            1089
```

<210> SEQ ID NO 3
<211> LENGTH: 309
<212> TYPE: DNA
<213> ORGANISM: Lolium perenne

<400> SEQUENCE: 3

```
catgcttcca gaaggagccg agacgtggcg acttcgtccg acgcgccgac tatctgcaca      60
cgccggctt ctcgtcgtgg gcgagtcagc agttacgggc tttccgccta ccaactcaca     120
cgtagcgccc tatcgtggcg cttgatcgat gcaacagcga tgcctatccc agctcctcaa     180
gctgcttata gtatgtcct cggccatcac tgcttacaca caaacacag ctacttatcg      240
cagtgtacta aacaagacgt actagctaga tttcgtgagg taaaatcagt gcaatatcac     300
ttgtgcaag                                                              309
```

<210> SEQ ID NO 4
<211> LENGTH: 762
<212> TYPE: PRT
<213> ORGANISM: Lolium perenne

<400> SEQUENCE: 4

```
Met Ala Ile Leu Gly Glu Leu Gly Thr Gln Val Leu Ile Pro Val Ala
  1               5                  10                  15

Gly Leu Ile Gly Ile Ala Phe Ala Val Ala Gln Trp Val Leu Val Ser
             20                  25                  30

Lys Val Lys Val Thr Pro Gly Ala Ala Thr Thr Ala Gly Gly Ala Lys
         35                  40                  45

Asn Gly Tyr Gly Asp Tyr Leu Ile Glu Glu Glu Glu Gly Leu Asn Asp
```

```
            50                  55                  60
His Asn Val Val Val Lys Cys Ala Glu Ile Gln Thr Ala Ile Ser Glu
 65                  70                  75                  80

Gly Ala Thr Ser Phe Leu Phe Thr Met Tyr Gln Tyr Val Gly Leu Phe
                 85                  90                  95

Met Val Phe Phe Ala Leu Leu Ile Phe Val Phe Leu Gly Ser Ile Glu
                100                 105                 110

Gly Phe Ser Thr Lys Ser Gln Pro Cys Thr Tyr Ser Thr Gly Thr Cys
                115                 120                 125

Lys Pro Ala Leu Tyr Thr Ala Leu Phe Ser Thr Ala Phe Leu Leu
130                 135                 140

Gly Ala Ile Thr Ser Leu Val Ser Gly Phe Leu Gly Met Lys Ile Ala
145                 150                 155                 160

Thr Tyr Ala Asn Ala Arg Thr Thr Leu Glu Ala Arg Lys Gly Val Gly
                165                 170                 175

Lys Ala Phe Ile Thr Ala Phe Arg Ser Gly Ala Val Met Gly Phe Leu
                180                 185                 190

Leu Ser Ser Gly Leu Val Val Leu Tyr Ile Thr Ile Asn Val Phe
                195                 200                 205

Lys Leu Tyr Tyr Gly Asp Asp Trp Glu Gly Leu Phe Glu Ser Ile Thr
210                 215                 220

Gly Tyr Gly Leu Gly Gly Ser Ser Met Ala Leu Phe Gly Arg Val Gly
225                 230                 235                 240

Gly Gly Ile Tyr Thr Lys Ala Ala Asp Val Gly Ala Asp Leu Val Gly
                245                 250                 255

Lys Val Glu Arg Asn Ile Pro Glu Asp Asp Pro Arg Asn Pro Ala Val
                260                 265                 270

Ile Ala Asp Asn Val Gly Asp Asn Val Gly Asp Ile Ala Gly Met Gly
                275                 280                 285

Ser Asp Leu Phe Gly Ser Tyr Ala Glu Ser Ser Cys Ala Ala Leu Val
                290                 295                 300

Val Ala Ser Ile Ser Ser Phe Gly Ile Ser His Asp Phe Thr Ala Met
305                 310                 315                 320

Cys Tyr Pro Leu Leu Val Ser Ser Val Gly Ile Ile Val Cys Leu Ile
                325                 330                 335

Thr Thr Leu Phe Ala Thr Asp Phe Phe Glu Ile Lys Ala Ala Asn Glu
                340                 345                 350

Ile Glu Pro Ala Leu Lys Lys Gln Leu Ile Ile Ser Thr Ala Leu Met
                355                 360                 365

Thr Val Gly Val Ala Ile Ile Ser Trp Leu Ala Leu Pro Ala Lys Phe
370                 375                 380

Thr Ile Phe Asn Phe Gly Ala Gln Lys Glu Val Ala Asn Trp Gly Leu
385                 390                 395                 400

Phe Phe Cys Val Gly Ile Gly Leu Trp Ala Gly Leu Ile Ile Gly Phe
                405                 410                 415

Val Thr Glu Tyr Tyr Thr Ser Asn Ala Tyr Ser Pro Val Gln Asp Val
                420                 425                 430

Ala Asp Ser Cys Arg Thr Gly Ala Ala Thr Asn Val Ile Phe Gly Leu
                435                 440                 445

Ala Leu Gly Tyr Lys Ser Val Ile Ile Pro Ile Phe Ala Ile Ala Val
450                 455                 460

Ser Ile Tyr Val Ser Phe Ser Ile Ala Ala Met Tyr Gly Ile Ala Met
465                 470                 475                 480
```

```
Ala Ala Leu Gly Met Leu Ser Thr Met Ala Thr Gly Leu Ala Ile Asp
            485                 490                 495

Ala Tyr Gly Pro Ile Ser Asp Asn Ala Gly Gly Ile Ala Glu Met Ala
        500                 505                 510

Gly Met Ser His Arg Ile Arg Glu Arg Thr Asp Ala Leu Asp Ala Ala
    515                 520                 525

Gly Asn Thr Thr Ala Ala Ile Gly Lys Gly Phe Ala Ile Gly Ser Ala
530                 535                 540

Ala Leu Val Ser Leu Ala Leu Phe Gly Ala Phe Val Ser Arg Ala Gly
545                 550                 555                 560

Val Gln Val Val Asp Val Leu Ser Pro Lys Val Phe Ile Gly Leu Leu
                565                 570                 575

Val Gly Ala Met Leu Pro Tyr Trp Phe Ser Ala Met Thr Met Lys Ser
            580                 585                 590

Val Gly Ser Ala Ala Leu Lys Met Val Glu Glu Val Arg Arg Gln Phe
        595                 600                 605

Asn Thr Ile Pro Gly Leu Met Glu Gly Thr Ala Lys Pro Asp Tyr Ala
    610                 615                 620

Thr Cys Val Lys Ile Ser Thr Asp Ala Ser Ile Lys Glu Met Ile Pro
625                 630                 635                 640

Pro Gly Ala Leu Val Met Leu Thr Pro Leu Ile Val Gly Thr Leu Phe
                645                 650                 655

Gly Val Glu Thr Leu Ser Gly Val Leu Ala Gly Ala Leu Val Ser Gly
            660                 665                 670

Val Gln Ile Ala Ile Ser Ala Ser Asn Thr Gly Gly Ala Trp Asp Asn
        675                 680                 685

Ala Lys Lys Tyr Ile Glu Ala Gly Asn Ser Asp His Ala Arg Ser Leu
    690                 695                 700

Gly Pro Lys Gly Ser Asp Cys His Lys Ala Ala Val Ile Gly Asp Thr
705                 710                 715                 720

Ile Gly Asp Pro Leu Lys Asp Thr Ser Gly Pro Ser Leu Asn Ile Leu
                725                 730                 735

Ile Lys Leu Met Ala Val Glu Ser Leu Val Phe Ala Pro Phe Phe Ala
            740                 745                 750

Thr Tyr Gly Gly Leu Leu Phe Lys Tyr Ile
        755                 760

<210> SEQ ID NO 5
<211> LENGTH: 2456
<212> TYPE: DNA
<213> ORGANISM: Lolium perenne

<400> SEQUENCE: 5
ccatggcgat cctcggggag ctcggcacgc aggtgctcat ccccgtcgcc ggcctcatcg      60
gcatcgcctt cgccgtcgcg cagtgggtgc tcgtctccaa ggtcaaggtc acgcccggcg     120
ccgccaccac cgcgggaggc gccaagaacg ggtatggtga ctacctcatc gaggaggagg     180
agggcctcaa cgaccacaac gtcgtcgtca agtgcgccga gatccagacc gccatctccg     240
aaggagcaac atcgtttctt ttcaccatgt accagtatgt tggcttattc atggttttct     300
tcgctctctt gatctttgta ttcctcggat cgatcgaggg attcagcaca aagagccagc     360
cctgcaccta tagcacggga acctgcaagc cagctcttta caccgctctc ttcagcactg     420
cggcttttct tgcttggagc catcacatct ctggtgtctg gtttccttgg gatgaagatc     480
```

```
ccacatatgc caatgccaga accacactgg aagcaaggaa gggtgttgga aaggcattca    540
tcaccgcttt ccggtctggt gcagttatgg gcttcttgct gtcatcaagt ggtctcgtgg    600
ttctttacat taccatcaac gtattcaagc tctactacgg tgatgactgg aaggtctttt    660
tcgagtctat cactgggtat ggtcttggtg gctcttccat ggctctcttc ggaagagttg    720
gtggaggtat ttacaccaag gctgctgatg tgggtgctga ccttgttggc aaagttgaaa    780
ggaacattcc tgaagatgac cccaggaacc cagctgtgat agctgacaac gttggtgaca    840
atgttggtga tatcgctgga atgggatcag atctcttcgg ttcatatgca gaatcttcct    900
gcgctgctct tgttgttgca tctatctcat cttttggaat cagccatgat ttcaccgcca    960
tgtgctaccc gctgcttgtg agctctgttg gcatcattgt ctgcttgatt accacactct   1020
ttgcaactga tttctttgag atcaaggctg caaatgaaat tgaacctgct ctaaagaagc   1080
agctcatcat ctccactgct ttaatgactg ttggtgttgc gataatcagc tggttggctc   1140
ttccagctaa gttcaccatc ttcaacttcg gtgcccagaa ggaagtggcc aactgggggct   1200 tgttcttctg tgttggaatt ggtctgtggg ctggtctcat tattgggttt gtgactgaat   1260
actacactag caatgcctac agccctgtgc aagatgttgc agattcctgc agaactggtg   1320
ctgctactaa cgtcatcttt gggcttgctc tgggttacaa gtcagttatc atcccaattt   1380
tcgctattgc tgtcagcatt tacgtcagct tctctattgc tgcaatgtat ggcattgcaa   1440
tggctgctct tggcatgcta agcacaatgg caactggtct tgctatcgat gcttatggtc   1500
ccattagtga caatgctggt ggaattgctg agatggccgg catgagccac agaatccgtg   1560
agagaactga tgctcttgat gctgctggaa acacaaccgc tgctattggg aagggcttcg   1620
ccattggatc agctgctctg gtgtcccctgg cacttttcgg tgcttttgtc agcagagccg   1680
gtgtgcaggt cgttgatgtc cttttctccaa aggtattcat tggcttgctt gttggagcca   1740
tgcttcccta ctggttctca gcgatgacca tgaagagtgt tggaagtgct gctctcaaga   1800
tggttgagga ggttcgcagg cagttcaaca ccattcctgg actgatggag ggaactgcca   1860
agcctgacta tgccacctgt gtcaagatct ctactgatgc ttctatcaag gagatgattc   1920
ctcctggtgc tttggttatg ctcacgcccc tcattgttgg gaccctcttt ggcgtggaaa   1980
ctctatctgg tgtttggct ggtgctcttg tttctggagt acagattgcc atctctgctt   2040
ccaacactgg tggtgcatgg gacaatgcaa agaagtacat tgaggctggc aacagtgatc   2100
atgctaggtc ccttggcccc aaggggtcag actgccacaa ggccgccgtg atcggtgaca   2160
ccattggaga ccccctcaag gacacatctg gcccatccct caacatcctc atcaagctca   2220
tggctgttga gtcccttgtg tttgcgccgt tcttgccac gtacggtggc ctgctgttca   2280
agtacatcta aagagcacag atgccaagtt aagcagaact acgatctatg acgtcatca    2340 tgaataactc cttgtccgtt cgtatgttgt gcactgttat ttttggttgt catgtcattc    2400
ccggattgtg ttacctttc tttggcctct tggaggtgtt acggtagtct cacgtg         2456
```

<210> SEQ ID NO 6
<211> LENGTH: 4679
<212> TYPE: DNA
<213> ORGANISM: Lolium perenne

<400> SEQUENCE: 6

```
ccatggcgat cctcggggag ctcggcacgc aggtgctcat ccccgtcgcc ggcctcatcg     60
gcatcgcctt cgccgtcgcg cagtgggtgc tcgtctccaa ggtcaaggtc acgcccggcg    120
ccgccaccac cgcgggaggc gccaagaacg ggtatggtga ctacctcatc gaggaggagg    180
```

-continued

| | |
|---|---|
| agggcctcaa cgaccacaac gtcgtcgtca agtgcgccga gatccagacc gccatctccg | 240 |
| aaggtgaccc tctctcccag atctgggccg gcactcgtcc gccccccgta gatccgcgcg | 300 |
| ttccccggcc gtacgagccg gggcctcttt cgccggggaa cttctccttc ggcgcattta | 360 |
| gaaagttgcg attttatgg ctgcccgttc cgcgcatatg ctcggtagat tcagcgctga | 420 |
| tctggtgagg gagctttcga attctaggtc ggcgagctcc ggcaaatgct gcctgcactt | 480 |
| ttcacaggct tttacagatg gataaaaacc acgataaa gagctcgact gtagcgacgc | 540 |
| caaaagttac tgctccttgt tgtatgcaca acaaagccaa atccgtgcgc tggagctttt | 600 |
| ggttcctgcg tgcgcgggcg ctcccaaata ctagtactgt cgttttctcg gcgaactatc | 660 |
| agctcctgtc atattttta gtcactcgct cctggccgct tccaaatctc catgatttcg | 720 |
| aagtgggctc ctgcgttact tttgcttctt attaggttgc ggctccacgt ggggctagca | 780 |
| gcagatccac atcttgcctt tttaaaatcc caaaattcat attagatgct tgtatttga | 840 |
| agctaaatcg aggttcaata aacacttctt ttaatgcttc atcaaccgct gcgcttgcta | 900 |
| cactatgtgt gtcggtgctg tagtaaagat gtagctttca gcccgtcgct ttctttctt | 960 |
| catatataat tagaaatgtt aacttgctcg tggaaggtgc ctgagggatc tgccaaacgc | 1020 |
| aacaagctcg acacgttgtg atttgcctaa ctcgacctttt actccactct cctgggtcta | 1080 |
| ggtagatcta ggcctgaaac gtcatgttct gggataagga tctcggccat ctgtcaccgc | 1140 |
| cgtctcagtt tgtccctagc attctgagat tgccatctta atcagccta ctaatgctta | 1200 |
| tcagatacgt gtcctatttt gtgggatgtg gtgattggtg tcaccaatat tgacctgagg | 1260 |
| cgtttcttcc ttgattggga tggatacttt tggtattgtc ttctaggatt ggatatgtag | 1320 |
| cttgctgctt tttcacttga ataaatctga aatagtagtg ggtggtgaca tttgtttgtc | 1380 |
| aatcgtgtca aattacttac taatttcaga aagatggcca gcattttaac ctgttatcaa | 1440 |
| ttgctgatgt tgcattttaa tattggtgtc acaaattcac caatattgac ctcaggcgtt | 1500 |
| tcttctttga ttgggatggc tactttgga actgtctgct aggattggat atgtagcttg | 1560 |
| ctccttttca cttatatgtg aaatagcaat gggtggtgac atttgtttgc caatcatgtc | 1620 |
| agtctgtagg tagatcatag tttgttaatt aagaatctca gaaagatgca gtttagacca | 1680 |
| aggctataat aatctatatt acctgcaccg ttaataagta taacaaaatg ctgatgttac | 1740 |
| tgaattctgt ttgagttaaa tcatatgatt tctgtgtaac aattatttct tattatgatg | 1800 |
| agcaggagca acatcgtttc ttttcaccat gtaccagtat gttggcttat tcatggtttt | 1860 |
| cttcgctctc ttgatctttg tattcctcgg atcgatcgag ggattcagca caaagagcca | 1920 |
| gccctgcacc tatagcacgg gaacctgcaa gccagctctt tacaccgctc tcttcagcac | 1980 |
| tgcggctttc ttgcttggag ccatcacatc tctggtgtct ggtttccttg ggatgaagat | 2040 |
| cgccacatat gccaatgcca gaaccacact ggaagcaagg aagggtgttg gaaaggcatt | 2100 |
| catcaccgct ttccggtctg gtgcagttat gggcttcttg ctgtcatcaa gtggtctcgt | 2160 |
| ggttctttac attaccatca acgtattcaa gctctactac ggtgatgact gggaaggtct | 2220 |
| tttcgagtct atcactgggt atggtcttgg tggctcttcc atggctctct tcggaagagt | 2280 |
| tggtggaggt atttacacca aggctgctga tgtgggtgct gaccttgttg gcaaagttga | 2340 |
| aaggaacatt cctgaagatg accccaggaa cccagctgtg agttctcctc tctctgcttt | 2400 |
| tggctaatag ttttaggcag attgtctgac aatgcttcta attatatggt gactatcatg | 2460 |
| gttcatgaat attgttgcta aacttggccc tcttgtttgc aggtgatagc tgacaacgtt | 2520 |

```
ggtgacaatg ttggtgatat cgctggaatg ggatcagatc tcttcggttc atatgcagaa    2580
tcttcctgcg ctgctcttgt tgttgcatct atctcatctt ttggaatcag ccatgatttc    2640
accgccatgt gctacccgct gcttgtgagc tctgttggca tcattgtctg cttgattacc    2700
acactctttg caactgattt ctttgagatc aaggctgcaa atgaaattga acctgctcta    2760
aagaagcagc tcatcatctc cactgcttta atgactgttg gtgttgcgat aatcagctgg    2820
ttggctcttc cagctaagtt caccatcttc aacttcggtg cccagaagga agtggccaac    2880
tggtaatata ttacttaatc tttgttactg tctgaaatgt gaactctctt ctgattatgt    2940
tgtcttgact tctcagggc ttgttcttct gtgttgaat tggtctgtgg gctggtctca    3000
ttattgggtt tgtgactgaa tactacacta gcaatgccta caggtgagca atttgttagt    3060
ttcagttata ttatttcttc atcattctat gtcagtgtct tatcatccaa attatttcct    3120
tgtcgcagcc ctgtgcaaga tgttgcagat tcctgcagaa ctggtgctgc tactaacgtc    3180
atctttgggc ttgctctggg ttacaagtca gttatcatcc caattttcgc tattgctgtc    3240
agcatttacg tcagcttctc tattgctgca atgtatggca ttgcaatggc tgctcttggc    3300
atgctaagca caatggcaac tggtcttgct atcgatgctt atggtcccat tagtgacaat    3360
gctggtggaa ttgctgagat ggccggcatg agccacagaa tccgtgagag aactgatgct    3420
cttgatgctg ctggaaacac aaccgctgct attgggaagg taaatttcct tgctgcatat    3480
ttgttggtta actcttctcc actactgtta tttatagcac atcatgaagt tataagcata    3540
tgataaatat gtgagctatt agattagcag gaattaggca gtgtgagatg gtttatagtg    3600
aaagctgctg tattagttat gtaactgtaa ccatgcatat aatgttgtag ggtttcgcca    3660
ttggatcagc tgctctggtg tccctggcac ttttcggtgc ttttgtcagc agagccggtg    3720
tgcaggtcgt tgatgtcctt tctccaaagg tattcattgg cttgcttgtt ggagccatgc    3780
ttccctactg gttctcagcg atgaccatga agagtgttgg aagtgctgct ctcaagatgg    3840
ttgaggaggt tcgcaggcag ttcaacacca ttcctggact gatggaggga actgccaagc    3900
ctgactatgc cacctgtgtc aagatctcta ctgatgcttc tatcaaggag atgattcctc    3960
ctggtgcttt ggttatgctc acgcccctca ttgttgggac cctcttggc gtggaaactc    4020 tatctggtgt tttggctggt gctcttgttt ctggagtaca ggtaccattg gatttctttt    4080
cttccttggt atatctgaat tgtaaattct aggcatttat tcattttcac ccttgcagat    4140
tgccatctct gcttccaaca ctggtggtgc atgggacaat gcaaagaagt acattgaggt    4200
aaatgttctt gaattcctga ttgattgaca ctgaggtata ttgactattg aggaaccaat    4260
gtttgtcatg tttctaactt tgtcatcacc ttctttgcta cttctcaggc tggcaacagt    4320
gatcatgcta ggtcccttgg ccccaagggg tcagactgcc acaaggccgc cgtgatcggt    4380
gacaccattg agacccccct caaggacaca tctggcccat ccctcaacat cctcatcaag    4440 ctcatgctg ttgagtccct tgtgtttgcg ccgttctttg ccacgtacgg tggcctgctg    4500
ttcaagtaca tctaaagagc acagatgcca agttaagcag aactacgatc tatggacgtc    4560
atcatgaata actccttgtc cgttcgtatg ttgtgcactg ttattttttg gttgtcatgt    4620
attcccggat tgtgttacct tttctttggc ctcttgaggt gttacggtag tctcacgtg    4679
```

<210> SEQ ID NO 7
<211> LENGTH: 4717
<212> TYPE: DNA
<213> ORGANISM: Lolium perenne

<400> SEQUENCE: 7

-continued

```
ccatggcgat cctcggggag ctcggcacgc aggtgctcat ccccgtcgcc ggcctcatcg      60
gcatcgcctt cgccgtcgcg cagtgggtgc tcgtctccaa ggtcaaggtc acgcccggcg     120
ccgccaccgc cgcaggggc gccaagaacg gctacggcga ctacctcatc gaggaggagg      180
agggcctcaa cgaccacaac gtcgtcgtca agtgcgccga gatccagacc gccatctccg     240
aaggtgacca ccgcatccct ccctcccctcc ctcccccag atctggcacg acctcgcac     300 gccgcccgta gatccgcgcg ttccacggcc gtacgacgat ggccgggctg attttctttc     360
cggcgcattt agaaagttgc gattttctg gctgcccgtt ccgcgcatat gctgctcggt      420
agagtctacc gctgatctgg tgagggaact ttcgaatttt tagctccgcg agctccccaa     480
atgctgcctg cactttccac aggctttacg aacagattga atagaaccac gggaaagctc     540
gactgtagcg acgcgaaaag ttactacccc ttgttgtatg cacaacaaag ccaaatccgt     600
gcgctcgagc ttttggttcc tgcgtgcgcg ggcgctccca aatactgtgt cgttttctcg     660
cccaactatc ttctcctgtc acattttta gtcactcact cccaggctcc cagctacctc      720
caaatctcca ggatttcgaa gtgggctcct gcgttacttt tgcttcttat taggtttctg     780
tttatgcggc tccacgtggg gcgagcagca gatccacatc ttgcctttt taaatctcaa      840 aattcataat agatgcttgt aatttgaagc taaatcgagg ttcaataaac acttctttta     900
atgcttcatc aaccggtgcg cttgctgcag tatgtgtgtc ggtgctctag tgaagatgta     960
gccttcagtg gcacatctac ccgtcgcttt cttttcttca tatataatca gaaatattaa    1020
cttgctcgtg gaaggtgcct gagggatctg ccaaacgcaa caagctcgac acgttgtgat    1080
ttgcctaact cgacctttac tccactctcc tgggtctagg tagatctagg cctgaaacgt    1140
catgttctgg gataaggatc tcggccatct gtcaccgccg tctcagtttg tccctagcat    1200
tctgagattg ccatcttaat cagcctaact aatgcttatc agatacgtgt cctattttgt    1260
gggatgtggt gattggtgtc accaatattg acctgaggcg tttcttcttt gattgggatg    1320 gatactttg gtattgtctt ctaggattgg atatgtagct tgctgctttt tcacttgaat     1380
aaatctgaaa tagtagtggg tggtgacatt tgtttgtcaa tcgtgtcaaa ttacttacta    1440
atttcagaaa gatggccagc atttaacct gttatcaatt gctgatgttg catttaata     1500 ttggtgtcac aaattcacca atattgacct caggcgtttc ttctttgatt gggatggcta    1560
cttttggaac tgtctgctag gattggatat gtagcttgct ccttttcact tatatgtgaa    1620
atagcaatgg gtggtgacat tggtttgcca atcgtgtcag tctgtaggta gatcatagtt    1680
tgttaattag gaatctcaga aagatgcagt ttagaccaag gctataataa tctatattac    1740
ctgcaccgtt aataagtata acaaaatgct gatgttactg aattctgttt gggttaaatc    1800
atatgatttc tgtgtaacaa ttatttctta ttatgatgag caggagcaac atcgtttctt    1860
ttcaccatgt accagtatgt tggcttattc atggctttct tcgctctctt gatctttgta    1920
ttcctcggat cgatcgaggg attcagcaca aagagccagc cctgcaccta tagcacggga    1980
acctgcaagc cagctcttta caccgctctc ttcagcactg cggctttctt gcttggagcc    2040
atcacatctc tggtgtctgg tttccttggg atgaagatcg ccacatatgc caatgccaga    2100
accacactgg aagcaaggaa gggtgttgga aaggcattca tcaccgcttt ccggtctggt    2160
gcagttatgg gcttcttgct gtcatcaagt ggtctcgtgg ttctttacat taccatcaac    2220
gtattcaagc tctactacgg tgatgactgg aaggtctttt cgagtctat cactgggtat     2280 ggtcttggtg gctcttccat ggctctcttc ggaagagttg gtggaggtat ttacaccaag    2340
```

```
gctgctgatg tgggtgctga ccttgttggc aaagttgaaa ggaacattcc tgaagatgac   2400
cccaggaacc cagctgtgag ttctcctctc tctgcttttg gctaatagtt ttaggcagat   2460
tgtctgacaa tgcttctaat tatatggtga ctatcatggt tcatgaatat tgttgctaaa   2520
cttggccctc ttgtttgcag gtgatagctg acaacgttgg tgacaatgtt ggtgatatcg   2580
ctggaatggg atcagatctc ttcggttcat atgcagaatc ttcctgcgct gctcttgttg   2640
ttgcatctat ctcatctttt ggaatcagcc atgatttcac cgccatgtgc tacccgctgc   2700
ttgtgagctc tgttggcatc attgtctgct tgattaccac actctttgca actgatttct   2760
ttgagatcaa ggctgcaaat gaaattgaac ctgctctaaa gaagcagctc atcatctcca   2820
ctgctttaat gactgttggt gttgcgataa tcagctggtt ggctcttcca gctaagttca   2880
ccatcttcaa cttcggtgcc cagaaggaag tggccaactg gtaatatatt acttaatctt   2940
tgttactgtc tgaaatgtga actctcttct gattatgttg tcttgacttc tcagggcttt   3000
gttcttctgt gttggaattg gtctgtgggc tggtctcatt attgggtttg tgactgaata   3060
ctacactagc aatgcctaca ggtgagcaat tgttagtttt cagttatatt atttcttcat   3120
cattctatgt cagtgtctta tcatccaaat tatttccttg tcgcagccct gtgcaagatg   3180
ttgcagattc ctgcagaact ggtgctgcta ctaacgtcat cttgggctt gctctgggtt   3240 acaagtcagt tatcatccca atttttcgcta ttgctgtcag catttacgtc agcttctcta   3300
ttgctgcaat gtatggcatt gcaatggctg ctcttggcat gctaagcaca atggcaactg   3360
gtcttgctat cgatgcttat ggtcccatta gtgacaatgc tggtggaatt gctgagatgg   3420
ccggcatgag ccacagaatc cgtgagagaa ctgatgctct tgatgctgct ggaaacacaa   3480
ccgctgctat tgggaaggta aatttccttg ctgcatattt gttggttaac tcttctccac   3540
tactgttatt tatagcacat catgaagtta taagcatatg ataaatatgt gagctattag   3600
attagcagga attaggcagt gtgagatggt ttatagtgaa agctgctgta ttagttatgt   3660
aactgtaacc atgcatataa tgttgtaggg tttcgccatt ggatcagctg ctctggtgtc   3720
cctggcactt ttcggtgctt ttgtcagcag agccggtgtg caggtcgttg atgtccttc   3780 tccaaaggta ttcattggct tgcttgttgg agccatgctt ccctactggt tctcagcgat   3840
gaccatgaag agtgttggaa gtgctgctct caagatggtt gaggaggttc gcaggcagtt   3900
caacaccatt cctggactga tggagggaac tgccaagcct gactatgcca cctgtgtcaa   3960
gatctctact gatgcttcta tcaaggagat gattcctcct ggtgctttgg ttatgctcac   4020
gcccctcatt gttgggaccc tctttggcgt ggaaactcta tctggtgttt tggctggtgc   4080
tcttgtttct ggagtacagg taccattgga tttctttct tccttggtat atctgaattg   4140
taaattctag gcatttattc attttcaccc ttgcagattc ccatctctgc ttccaacact   4200
ggtggtgcat gggacaatgc aaagaagtac attgaggtaa atgttcttga attcctgatt   4260
gattgacact gaggtatatt gactattgag gaaccaatgt tgtcatgtt tctaactttg   4320 tcatcacctt ctttgctact tctcaggctg gcaacagtga tcatgctagg tcccttggcc   4380 ccaagggtc agactgccac aaggccgccg tgatcggtga caccattgga gaccccctca   4440
aggacacatc tggcccatcc ctcaacatcc tcatcaagct catggctgtt gagtcccttg   4500
tgtttgcgcc gttccttgcc acgtacggtg gcctgctgtt caagtacatc taaagagcac   4560
agatgccaag ttaagcagaa ctacgatcta tggacgtcat catgaataac tccttgtccg   4620
ttcgtatgtt gtgcactgtt attttttggtt gtcatgttat tcccggattg tgttaccttt   4680
tctttggcct cttgaggtgt tacggtagtc tcacgtg                            4717
```

```
<210> SEQ ID NO 8
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 8
cgtaactgct gactcgccca cgacgagaag                               30

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 9
gtctcggctc cttctggaag catgg                                    25

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 10
ctgtgccgtg caaaaatg                                            18

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
tgcactgatt ttacctcacg                                          20

<210> SEQ ID NO 12
<211> LENGTH: 47
<212> TYPE: DNA
<213> ORGANISM: Artificial Sequence
<220> FEATURE:
<223> OTHER INFORMATION: Oligonucleotide primer

<400> SEQUENCE: 12
aatctagagg cgcgccgggc tggtaaaaca aatataagta ttaatat            47

<210> SEQ ID NO 13
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 13
aatctagagc acaagtgata ttgcactgat tttacctcac                    40

<210> SEQ ID NO 14
<211> LENGTH: 25
<212> TYPE: DNA
<213> ORGANISM: Artificial Sequence
<220> FEATURE:
```

```
<223> OTHER INFORMATION: Oligonucleotide primer

<400> SEQUENCE: 14
ccatggcgat cctcggggag ctcgg                                        25

<210> SEQ ID NO 15
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 15
aatctagacc atggcgatcc tcggggagct cgg                               33

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 16
gcaggaagtt tgctcaggca gcta                                         24

<210> SEQ ID NO 17
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 17
aaggcgcgcc gcaggaagtt tgctcaggca gcta                              34

<210> SEQ ID NO 18
<211> LENGTH: 6958
<212> TYPE: DNA
<213> ORGANISM: Artificial Sequence
<220> FEATURE:
<223> OTHER INFORMATION: Expression vector containing the promoter from
      Lolium perenne fused to a gene of interest

<400> SEQUENCE: 18
ggcgcgccgg gctggtaaaa caaatataag tattaatata aatataatac aatagaagga     60
aaataaataa aatttccctc tgtgccgtgc aaaaatgcac ggcaatgggt tggcccgcac    120
ggcaaaggca tcgttgccgt gtccacggca atgggttggc ccgcacggca aaggcatcgt    180
tgccgtgtcc acgtctttgc cgtgcgcctt ggctctatct ttgccgtgaa gcgttctttg    240
ccgtgtgcct tttatttctt tgccgtggga tgctgccttt gccgagcgct gagctggcgc    300
tttgccgtgc gcgtattgtt tgccgtgcgt cctcccagag ctgtacggca agaattcat    360 tgccgtgcac gaggcacacg ggaaagaagt ttcgcatggc aaagggcgct gacagcacac    420
ggcaaagagc ccggcacggc attgagcttt ttttcccgta atgatagacg gcataatata    480
atggacgcac atgctgatgt caggatgtca cccactcatc ctagtatttg tgggacgtga    540 attcttgtg agatgggcaa tgggatgtga acaaaataag ttttgtacta gtagataaac    600
atttttaccc ataaacaatt gttctgtatt gaatgaaaaa ttattttgta ctggatgaaa    660
atcttctgag taactgtgta agattaacat gaatcaagag acaaatccaa tggctacaaa    720
gtcaactaat acttgttaaa agttccgata cttaaaatta tcaaaactga tatatagaat    780
```

```
attgcccatc tcgccaccgt gctagtttaa cagacgatgg acgaatatca gtcttgtatt    840
ggataatcga tgcatgcgag ctatcggtca cctgtccatg cttccagaag gagccgagac    900
gtggcgactt cgtccgacgc gccgactatc tgcacacgcc cggcttctcg tcgtgggcga    960
gtcagcagtc acaggctttc cgcctaccaa ctcacacgta gcgccctatc gtggcgcttg   1020
atcgatgcaa cagcgatgcc tatcccagct cctcaagctg cttataagta tgtcctcggc   1080
catcactgct tacacaacaa acacagctac ttatcgcagt gtactaaaca agacgtacta   1140
gctagatttc gtgaggtaaa atcagtgcaa tatcacttgt gctctagacc atggcgatcc   1200
tcggggagct cggcacgcag gtgctcatcc ccgtcgccgg cctcatcggc atcgccttcg   1260
ccgtcgcgca gtgggtgctc gtctccaagg tcaaggtcac gcccggcgca gccaccgccg   1320
ccgggggcgc caagaacgga tacgcgact acctcatcga ggaggaggag ggcctcaacg    1380
accacaacgt cgtcgtcaag tgcgccgaga tccagaccgc catctccgaa ggtgaccacc   1440
gcctacctcc ctccctcccc cagatctggc acggcactcg cccgccgccc gtagatccgc   1500
gcgtccacgg ccgtacgagc cggggactct ttcgccggcg gaactttttt ttcggcgcat   1560
ttagaaagtt gcgattttt tctggctgcc cgttccgcgc atatgctcgg tagattctac   1620
cgctgatctg gtgagggagc tttcgaattt tagctcggcg agctccccaa atgttgcctg   1680
cactctccac aggctttacg aacagatgga atggaaccac gggaaagctc gactgtagcg   1740
acgcgaaaag ttactacccc ttgttgtatg caaaaaaaag ccaaatccgt gcgctggagc   1800
ttttggttcc tgcgtgcgcg ggcgctccca aatactagtg tcgttttctc ggccaactat   1860
cttctcctgt gatatttttt agtcactcac tcccactctc ccaggctccc agctacctcc   1920
aaatctccag gattacgaag tgggctcctg cgttactttt gcttcttagt attaggtttc   1980
cgtttatgcg gctccacgtg gggcgagcag cagatccaca tcttgccttt tttaattctc   2040
aaaattcata ttactagtgt atatgcttga atttctagta actacatcga ggcttcaata   2100
aacacttctt ttaatgcttc atcaaccgct gcgcttgcta cactatgtgt gtcggtgctc   2160
tagtaaagat gtagcttatc ccgcgggcac atctacccgt cgctttcatt tcttcatata   2220
taatcacaaa tgttaacttg ctcgtggaag gtgcgtgacg gatctgccaa acgcaagaag   2280
ctcgacacgt tgtgatttgc ctaactcaac ctttactcca ctctcctggg tctaggtaga   2340
tctaggcctg aaacgtcatg ttctgggata aggatatcag ccatctgtca ccgatgcgtc   2400
agtttgtccc tagccttctg agattaatca gcttaatgct tatctgatac gtgtcctatt   2460
ttgtgggatt cggtgattag tgtcaccaat attgacctga ggggattctt ctttgattgg   2520
gatggacaca cttttggaat tgtcttctag gattggatat gtaccttgct gttttttttac   2580
ttgaataaat ctgaaatagc agtgggtggt gacaattgtt tgtcaaattt gtcaaattac   2640
ctactaattt cagaaagatg gccagcattt taatctgtta tcaattcctg atgttgcatt   2700
ttaatatcgg tgtcacaaac tcaccaatat tgacctcaga cgtttcttct ttgattggga   2760
cggctacttt tggaactgtc tgctaggatt ggatatgtag cttgctcctt ttcacttata   2820
tgtgaaatag caatgggtgg tgacattggt ttgccaatcg tgtcagtctg taggtagatc   2880
atagtttgtt aattaggaat ctcagaaaga tgcagtttag accaaggcta taataatcta   2940
tattacctgc accgttaata agtataacaa aatgctgatg ttactgaatt ctgtttgagt   3000
taaatcatat gatttctgtg taacaattat ttcttattat gatgagcagg agcaacatcg   3060
tttcttttca ccatgtacca gtatgttggc ttattcatgg ttttcttcgc tctcttgatc   3120
tttgtattcc tcggatcgat cgagggattc agcacaaaga gccagccctg cacctatagc   3180
```

```
acgggaacct gcaagccagc tctttacacc gctctcttca gcactgcggc tttcttgctt      3240
ggagccatca catctctggt gtctggtttc cttgggatga agatcgccac atatgccaat      3300
gccagaacca cactgaaagc aaggaagggt gttggaaagg cattcatcac cgctttccgg      3360
tctggtgcag ttatgggctt cttgctgtca tcaagtggtc tcgtggttct ttacattacc      3420
atcaacgtat tcaagctcta ctacggtgat gactgggaag gtcttttga atctatcact       3480 gggtatggtc ttggtggctc ttccatggct ctcttcggaa gagttggtgg aggtatttac      3540
accaaggctg ccgatgtggg tgctgacctt gttggcaaag ttgaaaggaa cattcctgaa      3600
gatgacccca ggaacccagc tgtgagttct cttctctctg ctcttggcta atagttttag      3660
gcatattgtc tgacaatgct tctaatcata tggtgactat catggttcat gaatgtcgtt      3720
tgctaaactt ggccccttg ttttcaggtg atagctgaca acgttggtga caatgttggt       3780
gatatcgctg gaatgggatc agatctcttc ggttcatacg cagaatcttc ctgcgctgct      3840
cttgttgttg catctatctc atcttttgga atcagccatg atttcaccgc gatgtgctac      3900
ccactgcttg tgagctctgt tggcatcatt gtctgcttga ttaccacact ctttgcaact      3960
gatttctttg agatcaaggc tgcaaatgaa attgaacctg ctctgaagaa gcagctcatc      4020
atctccactg ctttaatgac tgttggtgtt gcgataatca gctggttggc tcttccagct      4080
aagttcacca tcttcaactt cggtgcccag aaggaagtgg ccaactggta atatattact      4140
caatctttgt ttctgtctga aatgtgaacc ctcttctgat tatgttgtct ggcttctca       4200 ggggcttgtt tttctgtgtg ggaattggac tgtgggctgg tctcattatt gggtttgtga      4260
ctgaatacta cactagcaat gcctacaggt gagcaatttg ttagtttcag ttatattatt      4320
tcttcatcat tctatgtcag tgtcttatca tcccaattat ttccttgtgg cagccctgtg      4380
caagatgttg cagattcctg cagaactggt gctgctacta acgtcatctt tgggcttgct      4440
ctgggttaca agtcagttat catcccaatt ttcgctattg ctgtcagcat ttacgtcagc      4500
ttctctattg ctgcaatgta cggcattgca atggctgctc ttggcatgct aagcacaatg      4560
gcaactggtc ttgctattga tgcttatggt cccattagtg acaatgctgg tggaattgct      4620
gagatggccg gcatgagcca cagaatccgt gagagaactg atgctcttga tgctgctgga      4680
aacacaaccg ctgctattgg gaaggtaaat ttccttgctg catatttgtt ggttaactct      4740
tctccacagc tgttatttat agcacatcag gaagttataa gcatatgata tatatgtgag      4800
ctactagatt agcaggaatt aggcagtgtg agatggttta gagtgaaagc tgctgtatta      4860
gtgatgtaac tgtaaccatg catataatgt tgtagggttt cgccattgga tcagctgctc      4920
tggtgtccct ggcactttc ggtgcttttg tcagcagagc cggtgtgcag gtcgttgatg      4980 tccttctcc aaaggtattc attggcttgc ttgttggagc catgcttccc tactggttct      5040
cagcgatgac catgaagagt gttggaagtg ctgctctcaa gatggttgag gaggttcgca      5100
ggcagttcaa caccattcct ggactgatgg agggaactgc caagcctgac tatgccacct      5160
gtgtcaagat ctctactgat gcttctatca aggagatgat tcctcctggt gctttggtta      5220
tgctcacgcc cctcattgtt gggaccctct ttggcgtgga aactctatct ggtgttttgg      5280
ctggtgctct tgtttctgga gtacaggtac cattggattt cttttcttcc ttggtatatc      5340
tgaattgtaa attctaggca tttattcatt ttcacccttg cagattgcca tctctgcttc      5400
caacactggt ggtgcatggg acaatgcaaa gaagtacatt gaggtaaatg ttcttgaatt      5460
cctgattgat tgacactgag gtatattgac tattgaggaa ccaatgtttg tcatgtttct      5520
```

```
aactttgtca tcaccttctt tgctacttct caggctggca acagtgatca tgctaggtcc    5580
cttggcccca aggggtcaga ctgccacaag gccgccgtga tcggtgacac cattggagac    5640
cccctcaagg acacatctgg cccatccctc aacatcctca tcaagctcat ggctgttgag    5700
tcccttgtgt ttgcgccgtt ctttgccacg tacggtggcc tgctgttcaa gtacatctaa    5760
agagcacaga tgccaagtta agcagaacta cgatctatgg acgtcatcat gaataactcc    5820
ttgtccgttc gtatgttgtg cactgttatt tttggttgtc atgttattcc cggattgtgt    5880 tacctttttct ttggcctctt ggaggtgtta cggtagtctc actcttacgg cttgtagctc    5940
catgtagaag agaccagatg ccctccctct ttggtatgtg tctggcaaat tttcctcgtc    6000
ccatgatgac gacgataatg ttgaactctt gaacaatgat atcatgattg ttgcatgtca    6060
cttgtagcaa gtcttgtttt tcacctaata tgtgtgtatc tgtcacatta tgactggcac    6120
aaaattgttg atgttttttgg cctaaaattg cactgattgt atgaactgct tcatctatag    6180
ttagctagat gctgatgtct tgggcataaa attgcactga ttgaacgaac tgcttcatct    6240
atagaagatc aacatgaaac tttgaattgt ttagttagct agatcggctg acttgcttga    6300
aatgttgaaa acccgtgggg gtatgcactt actgctgatc aaccaccttta gttcctgttt    6360 ggaatattgg aacgttctcc tgtcttgttg aaatgcttgt aaattatggg tttgtattta    6420
ctcgtaggga acatactaat tacaatgaaa tttgtgcttc ccaaaagttt atatatagat    6480
catcaggaag cttcctccga aacttttgac ccatttctgc ttgtcttttc actatgtttc    6540
ccactcaaag tactgaaggt cctgaacttg aaggaatctg attcatctct cttctgcacc    6600
attatcaatt tcccctccaa cctatcacag ttataacaca acaccgcaca cttttccttgg   6660 gatggacacg cttagctatc catcacaaca aagaatctca caaataaaa cctaactaca    6720 agcagggca cggacgtatg ggatgtgagc aaaaacaatg gagtaaggtg caatgacaat    6780
gtgctgcgcg gcagcaactc tgacaggctc catcctgggg atgttcccat ctgcatcagt    6840
gaccaaggcc ctgccattca gcatcatcac ctggctctgg atatcgccgt ctttgggggt    6900
gagatggtac tcctctctca tggcgctagc tgcctgagca aacttcctgc ggcgcgcc     6958
```

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
gtgtgcaggt cgttgatgtc                                                 20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 20
gcaccaggag gaatcatctc                                                 20

<210> SEQ ID NO 21
<211> LENGTH: 5
<212> TYPE: DNA
<213> ORGANISM: Artificial Sequence
<220> FEATURE:
<223> OTHER INFORMATION: cis element sequence

```
<400> SEQUENCE: 21 ccgac                                                                        5

<210> SEQ ID NO 22
<211> LENGTH: 6
<212> TYPE: DNA
<213> ORGANISM: Artificial Sequence
<220> FEATURE:
<223> OTHER INFORMATION: cis element sequence

<400> SEQUENCE: 22 gacgtg                                                                       6

<210> SEQ ID NO 23
<211> LENGTH: 6
<212> TYPE: DNA
<213> ORGANISM: Artificial Sequence
<220> FEATURE:
<223> OTHER INFORMATION: cis element sequence

<400> SEQUENCE: 23 cacctg                                                                       6

<210> SEQ ID NO 24
<211> LENGTH: 6
<212> TYPE: DNA
<213> ORGANISM: Artificial Sequence
<220> FEATURE:
<223> OTHER INFORMATION: coding strand

<400> SEQUENCE: 24 gatcta                                                                       6

<210> SEQ ID NO 25
<211> LENGTH: 6
<212> TYPE: RNA
<213> ORGANISM: Artificial Sequence
<220> FEATURE:
<223> OTHER INFORMATION: mRNA of coding strand

<400> SEQUENCE: 25 cuagau                                                                       6

<210> SEQ ID NO 26
<211> LENGTH: 6
<212> TYPE: DNA
<213> ORGANISM: Artificial Sequence
<220> FEATURE:
<223> OTHER INFORMATION: antisense strand

<400> SEQUENCE: 26 ctagat                                                                       6

<210> SEQ ID NO 27
<211> LENGTH: 7
<212> TYPE: RNA
<213> ORGANISM: Artificial Sequence
<220> FEATURE:
<223> OTHER INFORMATION: antisense RNA

<400> SEQUENCE: 27 gaucucg                                                                      7

<210> SEQ ID NO 28
```

-continued

```
<211> LENGTH: 6
<212> TYPE: DNA
<213> ORGANISM: Artificial Sequence
<220> FEATURE:
<223> OTHER INFORMATION: first half of inverted repeat

<400> SEQUENCE: 28 gatcta                                                                 6

<210> SEQ ID NO 29
<211> LENGTH: 6
<212> TYPE: DNA
<213> ORGANISM: Artificial Sequence
<220> FEATURE:
<223> OTHER INFORMATION: second half of inverted repeat

<400> SEQUENCE: 29 tagatc                                                                 6

<210> SEQ ID NO 30
<211> LENGTH: 6
<212> TYPE: DNA
<213> ORGANISM: Artificial Sequence
<220> FEATURE:
<223> OTHER INFORMATION: first half of inverted repeat

<400> SEQUENCE: 30 ctagat                                                                 6

<210> SEQ ID NO 31
<211> LENGTH: 6
<212> TYPE: DNA
<213> ORGANISM: Artificial Sequence
<220> FEATURE:
<223> OTHER INFORMATION: second half of inverted repeat

<400> SEQUENCE: 31 atctag                                                                 6
```

REGULATION OF GENE EXPRESSION IN PLANTS

REFERENCE TO RELATED APPLICATIONS

The present application claims priority to New Zealand patent application number 541710 filed Aug. 9, 2005, which is incorporated by reference in its entirety.

TECHNICAL FIELD

The present invention relates to the isolation and use of the polynucleotides for the control of gene expression in plants.

BACKGROUND ART

An important for goal for agriculture is to produce plants with agronomically important traits. Recent advances in genetic manipulation provide the tools to transform plants to contain and express foreign genes. This has led to the development of plants capable of expressing pharmaceuticals and other chemicals, plants with increased pest resistance, increased stress tolerance and many other beneficial traits.

It is often desirable to control expression of a polynucleotide of interest, in a particular tissue, at a particular developmental stage, or under particular conditions, in which the polynucleotide is not normally expressed. The polynucleotide of interest may encode a protein or alternatively may be intended to effect silencing of a corresponding target gene.

Plant promoter sequences are useful in genetic manipulation for directing such spatial, temporal and inducible expression of polynucleotides in transgenic plants. To achieve this, a genetic construct is often introduced into a plant cell or plant. Typically such constructs include a plant promoter operably linked to the polynucleotide sequence of interest. Such a promoter need not normally be associated with the gene of interest. Once transformed, the promoter controls expression of the operably linked polynucleotide of interest thus leading to the desired transgene expression and resulting desired phenotypic characteristics in the plant.

Promoters used in genetic manipulation are typically derived from the 5' un-transcribed region of genes and contain regulatory elements that are necessary to control expression of the operably linked polynucleotide. Promoters useful for plant biotechnology can be classified depending on when and where they direct expression. For example promoters may be tissue specific or constitutive (capable of transcribing sequences in multiple tissues). Other classes of promoters include inducible promoters that can be triggered on external stimuli such as environmental, and chemical stimuli.

It would be beneficial to have a variety of promoters available in order to ensure that transgenes are transcribed efficiently in the right tissues, at an appropriate stage of growth or development. Additionally it may be desirable to direct a gene expression in response to certain environmental or chemicals signals.

Promoters that are responsive to stresses, including mechanical and environmental stresses may be of particular benefit. It has been shown that constitutive expression of stress-inducible genes has negative impact on plant growth and development in the absence of the stress (Kasuga et al. 1999 Nature Biotechnology 17:287-291). Stress responsive promoters may therefore be particularly useful for driving expression of stress-inducible or stress-protective genes. If such genes are linked to a stress responsive promoter such genes are only induced under the appropriate stress conditions.

Perennial ryegrass (*Lolium perenne L*) is the major grass species grown in New Zealand and other temperate climates throughout the world. Valuable traits that may be improved by genetic manipulation of perennial ryegrass include stress tolerance, disease tolerance and nutritional quality. Genetic manipulation of such traits in perennial ryegrass is limited by the availability of promoters, particularly stress-responsive promoters, capable of appropriately controlling the expression of genes of interest.

It is therefore an object of the present invention to provide a stress responsive promoter from ryegrass useful for controlling expression of genes in plants or at least to provide a useful choice.

SUMMARY OF THE INVENTION

In one aspect the invention provides an isolated stress-responsive promoter polynucleotide comprising:
a) the sequence of SEQ ID NO:1 or SEQ ID NO:2;
b) a variant of the sequence of SEQ ID NO:1 or SEQ ID NO:2;
c) a fragment of the sequence of SEQ ID NO:1 or SEQ ID NO:2;
d) a fragment of the sequence of b);
e) a variant of the sequence of c); or
f) the complement of any one of a) to e).

In one embodiment the isolated stress-responsive promoter polynucleotide comprises:
a) the sequence of SEQ ID NO:1 or SEQ ID NO:2;
b) a sequence with at least 70% identity to the sequence of SEQ ID NO:1 or SEQ ID NO:2;
c) at least 50 contiguous nucleotides of the sequence of SEQ ID NO:1 or SEQ ID NO: 2;
d) at least 50 contiguous nucleotides of the sequence of b);
e) a sequence with at least 70% identity to the sequence of c); or
f) the complement of any one of a) to e).

In a further embodiment the stress is dehydration stress.
In a further embodiment the stress is mechanical stress.
In a further aspect the invention provides a genetic construct comprising a promoter polynucleotide of the invention.
In one embodiment the promoter polynucleotide is operably linked to a polynucleotide sequence of interest.
In a further embodiment the polynucleotide sequence of interest encodes a stress-protective polypeptide.
In a further embodiment the stress-protective polypeptide is a vacuolar pyrophosphatase.
In a further embodiment the vacuolar pyrophosphatase comprises the sequence of SEQ ID NO:4 or variant thereof.
In a further embodiment the vacuolar pyrophosphatase comprises a sequence with at least 70% sequence identity to the amino acid sequence of SEQ ID NO:4
In a further embodiment the vacuolar pyrophosphatase comprises the sequence of SEQ ID NO:4.
In a further embodiment the vacuolar pyrophosphatase comprises the sequence of SEQ ID NO:5 or variant thereof.
In a further embodiment the polynucleotide sequence encoding a vacuolar pyrophosphatase comprises a sequence with at least 70% identity to the coding sequence of SEQ ID NO:5.
In a further embodiment the polynucleotide sequence encoding a vacuolar pyrophosphatase comprises the coding sequence of SEQ ID NO:5.
In a further embodiment the polynucleotide sequence encoding a vacuolar pyrophosphatase comprises a sequence with at least 70% identity to the coding sequence of SEQ ID NO:6.

In a further embodiment the polynucleotide sequence encoding a vacuolar pyrophosphatase comprises the coding sequence of SEQ ID NO:6.

In a further aspect the invention provides a vector comprising a genetic construct of the invention.

In a further aspect the invention provides a host cell transformed with a promoter polynucleotide of the invention.

In a further aspect the invention provides a host cell transformed with a genetic construct of the invention.

In a further aspect the invention provides a plant cell transformed with the promoter polynucleotide of the invention.

In a further aspect the invention provides a plant cell transformed with a genetic construct of the invention.

In a further aspect the invention provides plant comprising a plant cell of the invention.

In a further aspect the invention provides a method for producing a plant cell or plant with modified expression of at least one polynucleotide sequence of interest, the method comprising the step of transforming plant cell or plant with a genetic construct of the invention.

In a further aspect the invention provides a method for modifying expression of at least one polynucleotide in a plant cell or plant, the method comprising:
  (a) providing a plant cell or plant transformed with genetic construct of the invention; and.
  (b) cultivating the transformed plant cell or plant under conditions conducive to the expression of the polynucleotide sequence of interest.

In a further aspect the invention provides a method for producing a plant with a modified phenotype, the method comprising the step of transforming plant cell or plant with a genetic construct of the invention.

In a further aspect the invention provides a method of modifying a phenotype in a plant, the method comprising:
  (a) providing a plant cell or plant transformed with genetic construct of the invention; and.
  (b) the cultivating the transgenic plant cell or plant under conditions conducive to the expression of the polynucleotide sequence of interest, wherein expression of the polynucleotide sequence of interest produces the modified phenotype.

In one embodiment the modified phenotype is increased tolerance to dehydration stress.

In a further embodiment the modified phenotype is increased tolerance to mechanical stress.

In a further aspect the invention provides a plant produced by a method of the invention.

In a further aspect the invention provides a seed, propagule, progeny or part of a plant, of the invention.

The polynucleotides or variants of the invention may be derived from any species and/or may be produced synthetically or recombinantly.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a from dicotyledonuous plant species.

In a further embodiment the polynucleotide or variant, is derived from a monocotyledonous plant species.

The polypeptide or variant, as encoded by the polynucleotidein the construct of the invention, may be derived from any species.

In one embodiment the polypeptide or variant, is derived from a plant species.

In a further embodiment the polypeptide or variant, is derived from a gymnosperm plant species.

In a further embodiment the polypeptide or variant, is derived from an angiosperm plant species.

In a further embodiment the polypeptide or variant, is derived from a from dicotyledonous plant species.

In a further embodiment the polypeptide or variant, is derived from a monocotyledonous plant species.

The plant cells and plants, of the invention may be derived from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferred dicotyledonous genera include: *Amygdalus, Anacardium, Anemone, Arachis, Brassica, Cajanus, Cannabis, Carthamus, Carya, Ceiba, Cicer, Claytonia, Coriandrum, Coronilla, Corydalis, Crotalaria, Cyclamen, Dentaria, Dicentra, Dolichos, Eranthis, Glycine, Gossypium, Helianthus, Lathyrus, Lens, Lespedeza, Linum, Lotus, Lupinus, Macadamia, Medicago, Melilotus, Mucuna, Olea, Onobiychis, Ornithopus, Oxalis, Papaver, Phaseolus, Phoenix, Pistacia, Pisum, Prunus, Pueraria, Ribes, Ricinus, Sesamum, Thalictrum, Theobroma, Trifolium, Trigonella, Vicia* and *Vigna.*

Preferred dicotyledonous species include: *Amygdalus communis, Anacardium occidentale, Anemone americana, Anemone occidentalis, Arachis hypogaea, Arachis hypogea, Brassica napus Rape, Brassica nigra, Brassica campestris, Cajanus cajan, Cajanus indicus, Cannabis sativa, Carthamus tinctorius, Carya illinionensis, Ceiba pentandra, Cicer arietinum, Claytonia exigua, Claytonia megarhiza, Coriandrum sativum, Coronilla varia, Corydalis flavula, Corydalis sempervirens, Crotalaria juncea, Cyclamen coum, Dentaria laciniata, Dicentra eximia, Dicentra formosa, Dolichos lablab, Eranthis hyemalis, Gossypium arboreum, Gossypium nanking, Gossypium barbadense, Gossypium herbaceum, Gossypium hirsutum, Glycine max, Glycine ussuriensis, Glycine gracilis, Helianthus annus, Lupinus angustifolius, Lupinus luteus, Lupinus mutabilis, Lespedeza sericea. Lespedeza striata, Lotus uliginosus, Lathyrus sativus, Lens culinaris, Lespedeza stipulacea, Linum usitatissimum, Lotus corniculatus, Lupinus albus, Medicago arborea, Medicago falcate, Medicago hispida, Medicago officinalis, Medicago sativa (alfalfa), Medicago tribuloides, Macadamia integrifolia, Medicago arabica, Melilotus albus, Mucuna pruriens, Olea europaea, Onobrychis viciifolia, Ornithopus sativus, Oxalis tuberosa, Phaseolus aureus, Prunus cerasifera, Prunus cerasus, Phaseolus coccineus, Prunus domestica, Phaseolus lunatus, Prunus, maheleb, Phaseolus mungo, Prunus. persica, Prunus. pseudocerasus, Phaseolus vilgaris, Papaver somniferum, Phaseolus acutlifolius. Phoenix dactylifera, Pistacia vera, Pisum sativum, Prunus amygdalus, Prunus armeniaca, Pueraria thunbergiana, Ribes nigrum, Ribes rubrum, Ribes grossularia, Ricinus communis, Sesamum indicum, Thalictrum dioicum, Thalictrum flavum, Thalictrum thalictroides, Theobroma cacao, Trifolium augustifolium, Trifolium diffusum, Trifolium hybridum, Trifolium incarnatum, Trifolium ingrescens, Trifolium pratense, Trifolium repens, Trifolium resupinatum, Trifolium subterraneum, Trifolium alexandrinum, Trigonella foenumgraecun, Vicia angustifolia, Vicia atropuipurea, Vicia calcarata, Vicia dasycarpa, Vicia ervilia, Vaccinium oxycoccos, Vicia pannonica,*

*Vigna sesquipedalis, Vigna sinensis, Vicia villosa, Vicia faba, Vicia sative* and *Vigna angularis*.

Preferred monocotyledonous genera include: *Agropyron, Allium, Alopecurus, Andropogon, Arrhenatherum, Asparagus, Avena, Bambusa, Bellavalia, Brimeura, Brodiaea, Bulbocodium, Bothrichloa, Bouteloua, Bromus, Calamovilfa, Camassia, Cenchrus, Chionodoxa, Chloris, Colchicum, Crocus, Cymbopogon, Cynodon, Cypripedium, Dactylis, Dichanthium, Digitaria, Elaeis, Eleusine, Eragrostis, Eremurus, Erythronium, Fagopyrum, Festuca, Fritillaria, Galanthus, Helianthus, Hordeum, Hyacinthus, Hvacinthoides, Ipheion, Iris, Leucojum, Liatris, Lolium, Lycoris, Miscanthis, Miscanthus x giganteus, Muscari, Ornithogalum, Oryza, Panicum, Paspalum, Pennisetum, Phalaris, Phleum, Poa, Puschkinia, Saccharum, Secale, Setaria, Sorghastrum, Sorghum, Triticum, Vanilla, X Triticosecale Triticale* and *Zea*.

Preferred monocotyledonous species include: *Agropyron cristatum, Agropyron desertorum, Agropyron elongatum, Agropyron intermedium, Agropyron smithii, Agropyron spicatum, Agropyron trachycaulum, Agropyron trichophorum, Allium ascalonicum, Allium cepa, Allium chinense, Allium porrum, Allium schoenoprasum, Alliumfistulosum, Allium sativum, Alopecurus pratensis, Andropogon gerardi, Andropogon Gerardii, Andropogon scoparious, Arrhenatherum elatius, Asparagus officinalis, Avena nuda, Avena sativa, Bambusa vulgaris, Bellevalia trifoliate, Brimeura amethystina, Brodiaea californica, Brodiaea coronaria, Brodiaea elegans, Bulbocodium versicolor, Bothrichloa barbinodis, Bothrichloa ischaemum, Bothrichloa saccharoides, Bouteloua curipendula, Bouteloua eriopoda, Bouteloua gracilis, Bromus erectus, Bromus inermis, Bromus riparius, Calamovilfa longifilia, Camassia scilloides, Cenchrus ciliaris, Chionodoxa forbesii, Chloris gayana, Colchicum autumnale, Crocus sativus, Cymbopogon nardus, Cynodon dactylon, Cypripedium acaule, Dactylis glomerata, Dichanthium annulatum, Dichanthium aristatum, Dichanthium sericeum, Digitaria decumbens, Digitaria smutsii, Elaeis guineensis, Elaeis oleifera, Eleusine coracan, Elymus angustus, Elymus junceus, Eragrostis curvula, Eragrostis tef, Eremurus robustus, Erythronium elgans, Erythronium helenae, Fagopyrum esculentum, Fagopyrum tataricum, Festuca arundinacea, Festuca ovina, Festuca pratensis, Festuca rubra, Fritillaria cirrhosa, Galanthus nivalis, Helianthus annuus sunflower, Hordeum distichum, Hordeum vulgare, Hyacinthus orientalis, Hyacinthoides hispanica, Hyacinthoides non-scripta, Ipheion sessile, Iris collettii, Iris danfordiae, Iris reticulate, Leucojum aestivum, Liatris cylindracea, Liatris elegans, Lilium longiflorum, Lolium multiflorum, Lolium perenne, Lycoris radiata, Miscanthis sinensis, Miscanthus x giganteus, Muscari armeniacum, Muscari macrocarpum, Narcissus pseudonarcissus, Ornithogalum montanum, Oryza sativa, Panicum italicium, Panicum maximum, Panicum miliaceum, Panicum purpurascens, Panicum virgatum, Panicum virgatum, Paspalum dilatatum, Paspalum notatum, Pennisetum clandestinum, Pennisetum glaucum, Pennisetum purpureum, Pennisetum spicatum, Phalaris arundinacea, Phleum bertolinii, Phleum pratense, Poa fendleriana, Poa pratensis, Poa nemoralis, Puschkinia scilloides, Saccharum officinarum, Saccharum robustum, Saccharum sinense, Saccharum spontaneum, Scilla autumnalis, Scilla peruviana, Secale cereale, Setaria italica, Setaria sphacelata, Sorghastrum nutans, Sorghum bicolor, Sorghum dochna, Sorghum halepense, Sorghum sudanense, Trillium grandiflorum, Triticum aestivum, Triticum dicoccum, Triticum durum, Triticum monococcum, Tilipa batalinii, Tulipa clusiana, Tulipa dasystemon, Tulipa gesneriana, Tulipa greigii, Tulipa kaufmanniana, Tulipa sylvestris, Tulipa turkestanica, Vanilla fragrans, X Triticosecale* and *Zea mays*.

Other preferred plants are forage plant species from a group comprising but not limited to the following genera: *Lolium, Festuca, Dactylis, Bromus, Trifolium, Medicago, Phleum, Phalaris, Holcus, Lotus, Plantago* and *Cichorium*.

Particularly preferred forage plants are from the genera *Lolium* and *Trifolium*. Particularly preferred species are *Lolium perenne* and *Trifolium repens*.

Particularly preferred monocotyledonous plant species are: *Lolium perenne* and *Oryza sativa*.

A particularly preferred plant species is *Lolium perenne*.

The term "plant" is intended to include a whole plant or any part of a plant, propagules and progeny of a plant.

The term 'propagule' means any part of a plant that may be used in reproduction or propagation, either sexual or asexual, including seeds and cuttings.

BRIEF DESCRIPTION OF THE DRAWINGS

FIG. 1 shows the promoter sequence of SEQ ID NO:1, with the addition of the methionine (ATG) translation initiation codon, and highlights the position of the promoter elements identified in the sequence discussed in Example 1.

DETAILED DESCRIPTION

Figure 2:
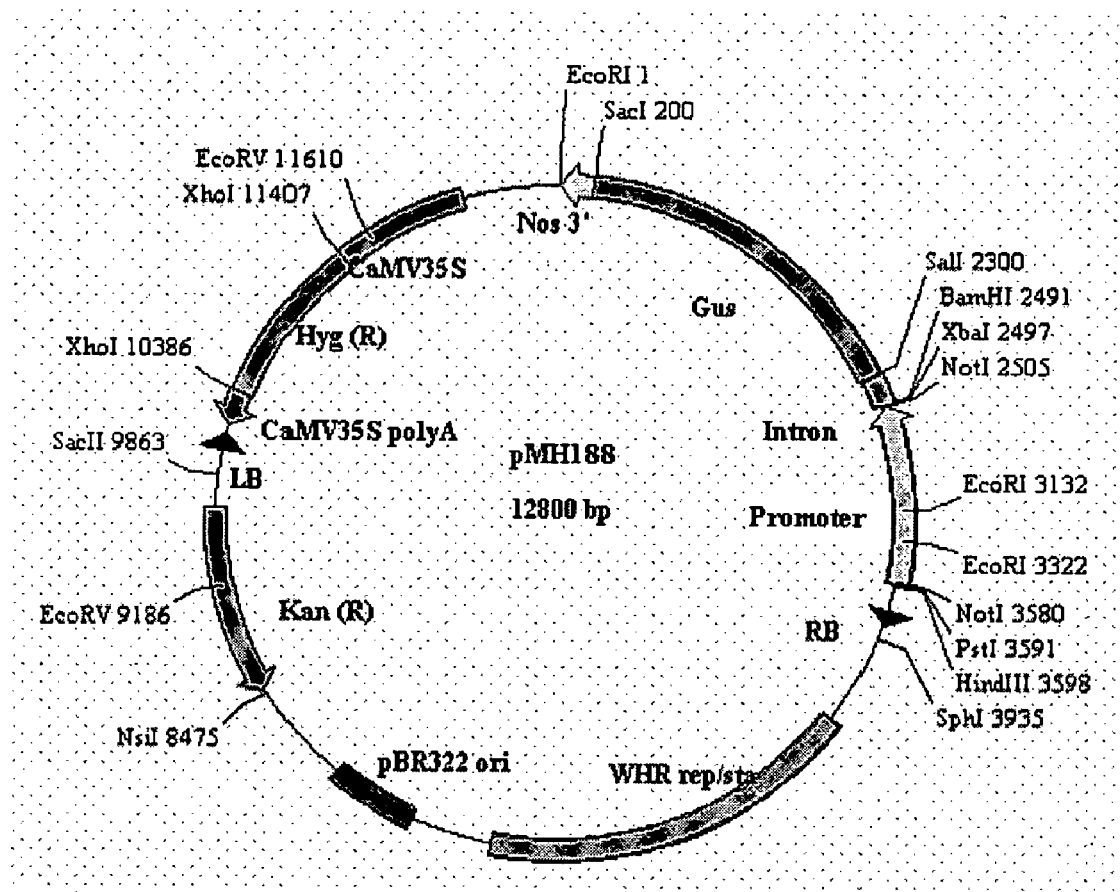
FIG. 2 shows a map of pMH188, a GUS reporter construct that was used to demonstrate the responsiveness of the promoter sequence SEQ ID NO:2 to mechanical and dehydration stress.

The applicants have identified a promoter polynucleotide sequence from ryegrass which is responsive to both mechanical and dehydration stress. The invention also provides variants and fragments of the promoter polynucleotide. The invention provides genetic constructs and vectors comprising the promoter polynucleotide sequences, and transgenic plant cells and transgenic plants comprising the promoter polynucleotide sequence, genetic constructs, or vectors of the invention.

The invention also provides methods for modifying expression of genes in plants and modifying phenotype in plants, and methods for producing plants with modified gene expression and modified phenotype. The invention further provides plants produced by the methods of the invention.

The term "stress-responsive", with reference to a promoter polynucleotide, means that the promoter polynucleotide is capable of up-regulating expression of an operably-linked polynucleotide in a plant in response to stress. The stress may be biotic including stresses caused by pathogen (bacterium, virus, yeast or fungus) infection, insect or herbivore feeding, and grazing by animals. The stress may also be abiotic including for example, stresses caused by excessive or insufficient availability of water, excessive or insufficient light intensity, extremes of temperature, synthetic chemicals such as herbicides and pesticides, excessive wind and mechanical damage.

Preferred stresses include dehydration stress and mechanical stress. Mechanical stress is intended to include stresses caused by herbivore and insect feeding, grazing animals and excessive wind action.

Dehydration stress is intended to include stress cause by periods of insufficient water availability during the life cycle of the plant.

"Stress-protective" proteins are those which when expressed improve the plants tolerance or resistance to stress. Stress-protective proteins include for example: bacterial L-aspartate-a-decarboxylase (Fouad and Rathinasabapathi, 2006, Plant Mol. Biol. 60: 495-505); alfalfa wxpl, (Zhang et al., 2005. Plant J. 42: 689-707); yeast sORF orthologs, e.g. YNR032C HUB1 (Kastenmayer et al., 2006. Genome Res. 16: 365-373); *Limonium latifolium* Beta-alanine N methyltransferase (Raman and Rathinasabapathi, 2003. Plant Physiology 132:1642-1651); alfalfa aldose/aldehyde reductase (ALR) (Oberschall et al., 2000. Plant J. 24:437-446.); Trehalose-6-P Synthase Gene (Garg et al., 2002. PNAS. 99: 15898-15903); CBF1 (Stockinger et al., 1997. Proc Natl Acad Sci USA 94: 1035-1040) and AVPI (Gaxioli et al. 2001 PNAs 98(20) 11,444-9).

A preferred stress-protective protein to be expressed by constructs of the invention, is the vacuolar pyrophosphatase of SEQ ID NO:4 encoded by the cDNA of SEQ ID NO:5 and genomic sequences of 6 and 7, and variants thereof.

The term "comprising" means "consisting at least in part of . . . ".

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that at least 15 nucleotides in length. The fragments of the invention comprise 15 nucleotides, preferably at least 20 nucleotides, more preferably at least 30 nucleotides, more preferably at least 40 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods.

The term "fragment" in relation to promoter polynucleotide sequences is intended to include sequences comprising cis-elements and regions of the promoter polynucleotide sequence capable of regulating expression of a polynucleotide sequence to which the fragment is operably linked. Preferably fragments of promoter polynucleotide sequences of the invention comprise at least 50, more preferably at least 100, more preferably at least 200, more preferably at least 300, more preferably at least 400, more preferably at least 500, more preferably at least 600, more preferably at least 700, more preferably at least 800, more preferably at least 900 and most preferably at least 1000 contiguous nucleotides of a promoter polynucleotide of the invention.

The term "primer" refers to a short polynucleotide, usually having a free 3'OH group, that is hybridized to a template and used for priming polymerization of a polynucleotide complementary to the template. Such a primer is preferably at least 5, more preferably at least 6, more preferably at least 7, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 nucleotides in length.

The term "probe" refers to a short polynucleotide that is used to detect a polynucleotide sequence, that is complementary to the probe, in a hybridization-based assay. The probe may consist of a "fragment" of a polynucleotide as defined herein. Preferably such a probe is at least 5, more preferably at least 10, more preferably at least 20, more preferably at least 30, more preferably at least 40, more preferably at least 50, more preferably at least 100, more preferably at least 200, more preferably at least 300, more preferably at least 400 and most preferably at least 500 nucleotides in length.

The term "derived from" with respect to polynucleotides of the invention being "derived from" a particular genera or species, means that the polynucleotide has the same sequence as a polynucleotide found naturally in that genera or species. The polynucleotide which is derived from a genera or species may therefore be produced synthetically or recombinantly.

Polypeptides and Fragments

The term "polypeptide", as used herein, encompasses amino acid chains of any length but preferably at least 5 amino acids, including full-length proteins, in which amino acid residues are linked by covalent peptide bonds. The polypeptides may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polypeptides disclosed being derived from a particular genera or species, means that the polypeptide has the same sequence as a polypeptide found naturally in that genera or species. The polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polynucleotides and polypeptides possess biological activities that are the same or similar to those of the inventive polynucleotides or polypeptides. The term "variant" with reference to polynucleotides and polypeptides encompasses all forms of polynucleotides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, more preferably at least 50 nucleotide positions, more preferably at least 100 nucleotide positions, more preferably at least 200 nucleotide positions, more preferably at least 300 nucleotide positions, more preferably at least 400 nucleotide positions, more preferably at least 500 nucleotide positions, more preferably at least 600 nucleotide positions, more preferably at least 700 nucleotide positions, more preferably at least 800 nucleotide positions, more preferably at least 900 nucleotide positions, more preferably at least 1000 nucleotide positions and most preferably over the entire length of the specified polynucleotide sequence.

Variant promoter polynucleotides of the invention preferably comprise at least one copy of one, more preferably at least one copy of two and most preferably at least one copy of three of the following cis-element sequences CCGAC(SEQ ID NO: 21), GACGTG (SEQ ID NO: 22), CACCTG(SEQ ID NO : 23).

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250). The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp.276-277). The European Bioinformatics Institute server also provides the facility to perform EMBOSS-needle global alignments between two sequences on line.

Alternatively the GAP program, which computes an optimal global alignment of two sequences without penalizing terminal gaps, may be used to calculate sequence identity. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available bl2seq program from the BLAST suite of programs (version 2.2.5 [November 2002]) from NCBI.

The similarity of polynucleotide sequences may be examined using the following unix command line parameters:

bl2seq-i nucleotideseq1-j nucleotideseq2-F F-p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$ more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides such as those in constructs of the invention encoding stress-protective protein, also encompasses polynucleotides that differ from the specified sequences but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also contemplated. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI via the tblastx algorithm as previously described.

Polypeptide Variants

The term "variant" with reference to polypeptides disclosed encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least %, more preferably at least 77%, more preferably at least 78%, more preferably at least 79%, more preferably at least 80%, more preferably at least 81%, more preferably at least. 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to the specified polypeptide sequences. Identity is found over a comparison window of at least 20 amino acid positions, preferably at least 50 amino acid positions, more preferably at least 100 amino acid positions, and most preferably over the entire length of the specified polypeptide.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle and GAP (Huang, X. (1994) On Global Sequence Alignment. Computer Applications in the Biosciences 10, 227-235.) as discussed above are also suitable global sequence alignment programs for calculating polypeptide sequence identity.

Polypeptide variants also encompass sequences that exhibit a degree of similarity to one or more of the specifically identified sequences that is likely to preserve the functional equivalence of those sequences and that could not reasonably be expected to have occurred by random chance. Such sequence similarity with respect to polypeptides may be determined using the publicly available bl2seq program from the BLAST suite of programs (version 2.2.5 [November 2002]) from NCBI. The similarity of polypeptide sequences may be examined using the following unix command line parameters:

bl2seq -i peptideseq1 -j peptideseq2 -F F -p blastp

Variant polypeptide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$ more preferably less than $1\times10^{-60}$, more preferably less than $1\times10^{-70}$, more preferably less than $1\times10^{-80}$ more preferably less than $1\times10^{-90}$ and most preferably less than $1\times10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain a promoter polynucleotide such as a promoter polynucleotide of the invention including the necessary elements that permit transcribing the insert polynucleotide molecule, and, optionally, translating the transcript into a polypeptide. The insert polynucleotide molecule may be derived from the host cell, or may be derived from a different cell or organism and/or may be a synthetic or recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter, such as a promoter polynucleotide sequence of the invention, functional in the host cell into which the construct will be transformed, b) the polynucleotide to be expressed, and c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" includes to untranslated sequences that are upstream of the translational start site and downstream of the translational stop site. These sequences are also referred to respectively as the 5' UTR and the 3' UTR. These sequences may include elements required for transcription initiation and termination and for regulation of translation efficiency. The term "noncoding" also includes intronic sequences within genomic clones.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to a polynucleotide sequence capable of regulating the expression of a polynucleotide sequence to which the promoter is operably linked. Promoters may comprise cis-initiator elements which specify the transcription initiation site and conserved boxes such as the TATA box, and motifs that are bound by transcription factors.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polynucleotides of the invention can be amplified using primers, as defined herein, derived from the polynucleotide sequences of the invention.

Further methods for isolating polynucleotides of the invention, or useful in the methods of the invention, include use of all or portions, of the polynucleotides set forth herein as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0. 5×SSC, 1% (w/v) sodium dodecyl sulfate, at 60° C. An optional further wash (for twenty minutes) can be conducted under conditions of 0.1X×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman Mass., 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

The promoter sequences disclosed may be characterized to identify fragments, such as cis-elements and regions, capable of regulating to expression of operably linked sequences, using techniques well-known to those skilled in the art. Such techniques include 5' and/or 3' deletion analysis, linker scanning analysis and various DNA footprinting techniques (for example Degenhardt et al., 1994 Plant Cell:6(8) 1123-34). Fragments include truncated versions of longer promoter sequences which may terminate (at the 3' end) at or close to the transcriptional start site. Methods for identifying the transcription start site of a promoter are well-known to those skilled in the art (discussed in Hashimoto et al., 2004, Nature Biotechnology 22, 1146-1149).

Promoter fragments can be tested for stress-responsiveness by techniques well-known to those skilled in the art. Techniques include operably-linking the promoter fragment to a reporter or other polynucleotide and measuring report activity or polynucleotide expressions in plants in response to stress. Such techniques are described in Example 2 of this specification.

Methods for Identifying Variants

Physical Methods

Variant polynucleotides may be identified using PCR-based methods (Mullis et al., Eds. 1994 The Polymerase Chain Reaction, Birkhauser).

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Computer Based Methods

Polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680 or T-COFFEE (Cedric Notredame, Desmond G. Higgins, Jaap Heringa, T-Coffee: A novel method for fast and accurate multiple sequence alignment, J. Mol. Biol. (2000) 302: 205-217))or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et. al., 1999, Nucleic Acids Res. 27, 215) is a method of identifying the functions of uncharacterized proteins translated from genomic or cDNA sequences. The PROSITE database contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Producing Constructs and Vectors

The genetic constructs of the present invention comprise one or more polynucleotide sequences of the invention and/or polynucleotides encoding polypeptides disclosed, and may be useful for transforming, for example, bacterial, fungal, insect, mammalian or particularly plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987 ; Ausubel et al., Current Protocols in Molecular Biology, Greene Publishing, 1987) for recombinant production of polypeptides. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide. Plants comprising such cells also form an aspect of the invention.

Methods for transforming plant cells, plants and portions thereof with polynucleotides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

The following are representative publications disclosing genetic transformation protocols that can be used to genetically transform the following plant species: Rice (Alam et al., 1999, Plant Cell Rep. 18, 572); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9,: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); perennial ryegrass (Bajaj et al., 2006, Plant Cell Rep. 25, 651); grasses (U.S. Pat. Nos. 5,187,073, 6.020, 539); peppermint (Niu et al., 1998, Plant Cell Rep. 17, 165); citrus plants (Pena et al., 1995, Plant Sci.104, 183); caraway (Krens et al., 1997, Plant Cell Rep, 17, 39); banana (U.S. Pat. No. 5,792,935); soybean (U.S. Pat. Nos. 5,416,011; 5,569,834; 5,824,877 ; 5,563,055 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); and cereals (U.S. Pat. No. 6,074,877). Other species are contemplated and suitable methods and protocols are available in the scientific literature for use by those skilled in the art.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. Strategies may also be designed to increase expression of a polynucleotide/polypeptide in response to an external stimuli, such as an environmental stimuli. Environmental stimuli may include environmental stresses such as mechanical (such as herbivore activity), dehydration, salinity and temperature stresses. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed or to reduce expression of a polynucleotide/polypeptide in response to an external stimuli. Such strategies are known as gene silencing strategies.

Genetic constructs for expression of genes in transgenic plants typically include promoters, such as promoter polynucleotides of the invention, for driving the expression of one or more cloned polynucleotide, terminators and selectable marker sequences to detect presence of the genetic construct in the transformed plant.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenbert. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide may include an antisense copy of a polynucleotide. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'           3'CTAGAT 5'
(SEQ ID NO: 24)       (SEQ ID NO: 26)
(coding strand)       (antisense strand)

3'CUAGAU 5'           5'GAUCUCG 3'
(SEQ ID NO: 25)       (SEQ ID NO: 27)
mRNA                  antisense RNA
```

Genetic constructs designed for gene silencing may also include an inverted repeat. An 'inverted repeat' is a sequence that is repeated where the second half of the repeat is in the complementary strand, e.g.,

5'-GATCTA (SEQ ID NO: 28) . . . TAGATC-3' SEQ ID NO: 29)

3'-CTAGAT (SEQ ID NO: 30) . . . ATCTAG-5' SEQ ID NO: 31)

```
5'-GATCTA.........TAGATC-3'

3'-CTAGAT.........ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a sequence operably-linked to promoter of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

Plants

A "transgenic" or transformed" plant refers to a plant which contains new genetic material as a result of genetic manipulation or transformation. The new genetic material may be derived from a plant of the same species as the resulting transgenic ot transformed plant or from a different species. A transformed plant includes a plant which is either stably or transiently transformed with new genetic material.

The plants of the invention may be grown and either self-ed or crossed with a different plant strain and the resulting hybrids, with the desired phenotypic characteristics, may be identified. Two or more generations may be grown. Plants resulting from such standard breeding approaches also form an aspect of the present invention.

EXAMPLES

The invention will now be illustrated with reference to the following non-limiting examples.

Example 1

Identification and Characterisation of the Ryegrass Stress Responsiveness Promoter Sequence Hypomethylated genomic DNA from *Lolium perenne* cv. Bronsyn was isolated and sequenced (Orion Genomics, St Louis). A hypomethylated genomic DNA sequence of 306 bp (SEQ ID NO:3) was identified as containing a 5' transcriptional regulatory region. Genome walking using oligonucleotide sequences (SEQ ID NO: 8 and 9) and a GenomeWalker Kit (Clontech) were used to extend the 5' transcriptional regulatory region of SEQ ID NO:3 to produce 5' regulatory region of 1175 bp (SEQ ID NO:1).

The applicants identified five cis-acting elements in the sequence of SEQ ID NO:1, that are likely to be required for the response to abiotic stresses. These elements are illustrated in FIG. 1. FIG. 1 also shows the position of the native translation initiation methionine ATG codon. Position of the elements with reference to FIG. 1 are as follows:

Two C-repeat binding sites (CCGAC; Stockinger et al., 1997, Proc Natl Acad Sci U S A. 94:1035-1040) are found at positions -264 and -272 upstream of the translation start codon and three abscisic acid response elements (GACGTG and CACCTG; Shinozaki and Yamaguchi-Shinozaki, 1997, Plant Physiol, 115: 327-335) at positions -288, -317 and -652 upstream of the translation start codon. The applicants also identified a putative TATA box at -123 upstream of the translation start codon.

Example 2

Demonstration of Stress-Responsiveness of the Ryegrass Promoter of the Invention Preparation of a Promoter Reporter Construct A 1,089 bp DNA sequence fragment was amplified by PCR from the sequence of SEQ ID NO:1 using oligonucleotide sequences (SEQ ID NO:10 and 11) and inserted into the cloning vector pGEM-T Easy (Promega). pGEM-T Easy harboring the promoter region was digested with NotI to release the DNA fragment. The NotI fragment was ligated in a 5'-3' orientation upstream of the GUS reporter gene (Jefferson R. A., et al., 1987. EMBO 6:3901-3907). This resulted in a transcriptional fusion between the ryegrass promoter and the reporter gene in the binary construct pMH188 (FIG. 2). The sequence of the ryegrass promoter in this construct is shown in SEQ ID NO:2.

Preparation of a Construct Including the Ryegrass Stress-Responsive Promoter Fused to a Gene of Interest A DNA fragment encompassing the promoter region was amplified from the sequence of SEQ ID NO:1 by PCR using oligonucleotide primer sequences (SEQ ID NO:12-13) and cloned into the pGEM-T Easy vector (Promega) according to manufacturer's instructions. A ryegrass genomic DNA fragment (SEQ ID NO:6) encoding vacuolar pyrophosphatase was amplified from ryegrass genomic DNA by PCR using oligonucleotide primer sequences (SEQ ID NO:14-17) and cloned into the pGEM-T Easy vector (Promega).

SEQ ID NO:5 is a cDNA corresponding to SEQ ID NO:6. SEQ ID NO:7 is a further genomic clone corresponding to SEQ ID NO:6. The ATG start codon is found at nucleotide position 3 in SEQ ID NO:5, 6 and 7. The stop codon (TAA) is found at nucleotide positions 2456, 4513 and 4551 in SEQ ID NO:5, 6 and 7 respectively.

Figure 4:
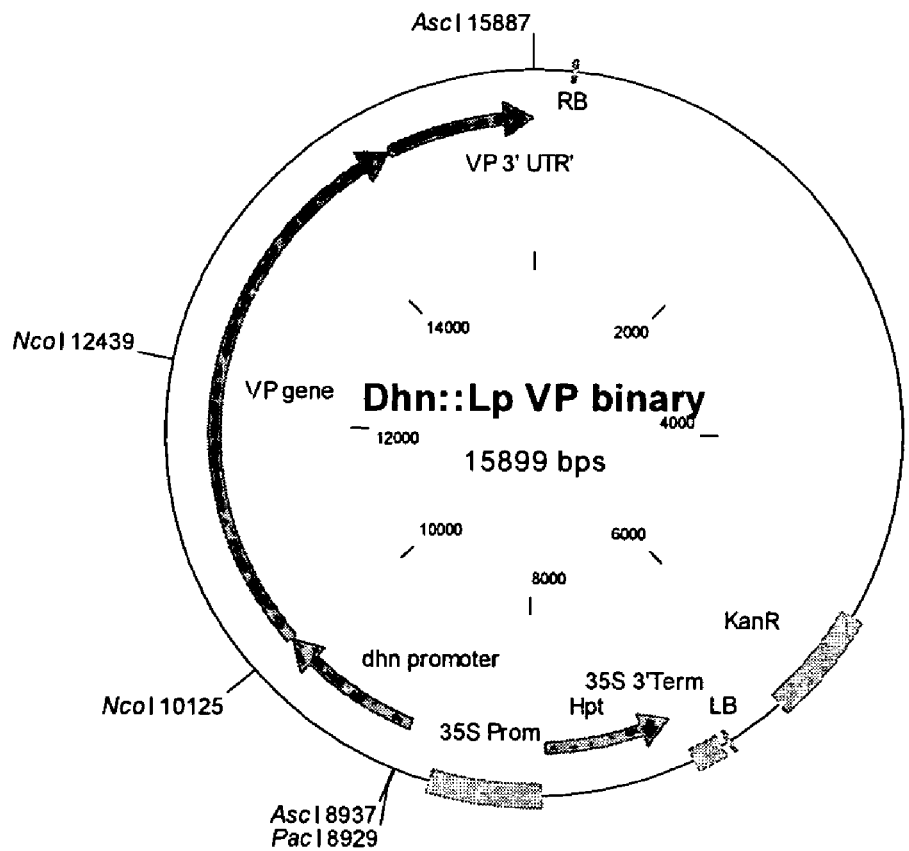
FIG. 4 shows a map of the binary construct comprising the promoter sequence of SEQ ID NO:1 fused to a sequence encoding vacuolar pyrophosphatase. The panel below shows nucleotide start and end numbers for the following elements in the construct: right border (RB, kanamycin resistance gene (kanR), left border (LB), Cauliflower Mosiac Virus 35S terminator (35S 3'term), hygromycin phosphotransferase gene (Hpt), Cauliflower Mosaic Virus 35S promoter (35S Prom), promoter of the invention (dhn promoter), vacuolar pyrophosphatase gene (VP gene) and vacuolar pyrophosphatase gene terminator (VP 3' UTR).

The promoter region was excised using XbaI and inserted in a 5'-3'orientation into the vector containing the ryegrass vacuolar pyrophosphatase genomic DNA fragment at the XbaI site. The expression cassette (SEQ ID NO:18) was excised using AscI and introduced into a binary plant transformation vector that had been linearised with AscI (see FIG. 4). The sequence of the ryegrass promoter in this vector is shown in SEQ ID NO:1.

Plant Transformation

Rice (*Oryza sativa* spp *japonica* cv. Niponbarre) was transformed using an immature embryo based system (Metahelix Life Sciences, India). Immature panicles, post-milky stage were used to source embryos. Freshly isolated immature embryos were co-cultivated with *Agrobacterium tumefaciens* (*A. tumefaciens*) harboring the promoter/GUS binary construct (pMH188) described above for 48-64 h. *A. tumefaciens* were eliminated by antibiotic treatment and the explants were transferred to selection medium where the transformed plant cells proliferate to give rise to uniformly transformed calli. The selection medium had a combination of 2,4-D and benzylaminopurine. After 3-4 weeks of selection, the calli were transferred to a regeneration medium containing increased cytokinin and decreased auxin concentration relative to the selection medium. Shoot and root were initiated in this medium. Plantlets were transferred to a glasshouse for hardening. Three primary transformed ($T_0$) plants were established in the glasshouse. Seed from the $T_0$ plants were grown to produce $T_1$ plants.

Perennial ryegrass (*Lolium perenne* L. cv. Tolosa) was transformed essentially as described in Bajaj et. al. (Plant Cell Reports 2006 25: 651-659). Embryogenic callus derived from mersitematic regions of the tillers of selected ryegrass lines and *Agrobacterium tumefaciens* strain EHA101 carrying a modified binary vector (FIG. 4) were used for transformation experiments. Embryogenic calli were immersed with overnight-grown *Agrobacterium* cultures for 30 minutes with continuous shaking. Calli resistant to hygromycin were selected after subculturing them on co-cultivation medium for 4 weeks. After selection, the resistant calli were subcultured on regeneration medium every 2 weeks until the plants regenerated. The regenerants that continued to grow after two or three rounds of selection proved to be stable transformants. Each regenerated plant was then multiplied on maintenance medium to produce clonal plantlets and subsequently rooted on MS medium without hormones. A rooted plant from each clone was transferred into contained glasshouse conditions while retaining a clonal counterpart in tissue culture as backup.

Demonstration of Stress-Responsiveness of the Promoter

Responsiveness of the Promoter to Mechanical Stimulus

Rice leaf sheaths from six week-old $T_1$, plants transformed with the promoter/reporter (GUS) construct described above were harvested and immediately subjected to mechanical stimulus by cutting transversely into 1-3 cm sections. Sections were then stained in GUS staining solution (Jefferson R. A., et al., 1987. EMBO 6:3901-3907). The time lapse between sampling and setting up staining was <15 min. GUS staining demonstrated beta-glucuronidase gene expression in cells at the cut end of the leaves as shown in FIG. 3a. No GUS activity was detected in non-wounded portion of the leaves. Increase in GUS activity at the cut site demonstrates responsiveness of the promoter to mechanical stress.

Responsiveness to the Promoter to Dehydration Stimulus

Figure 3:
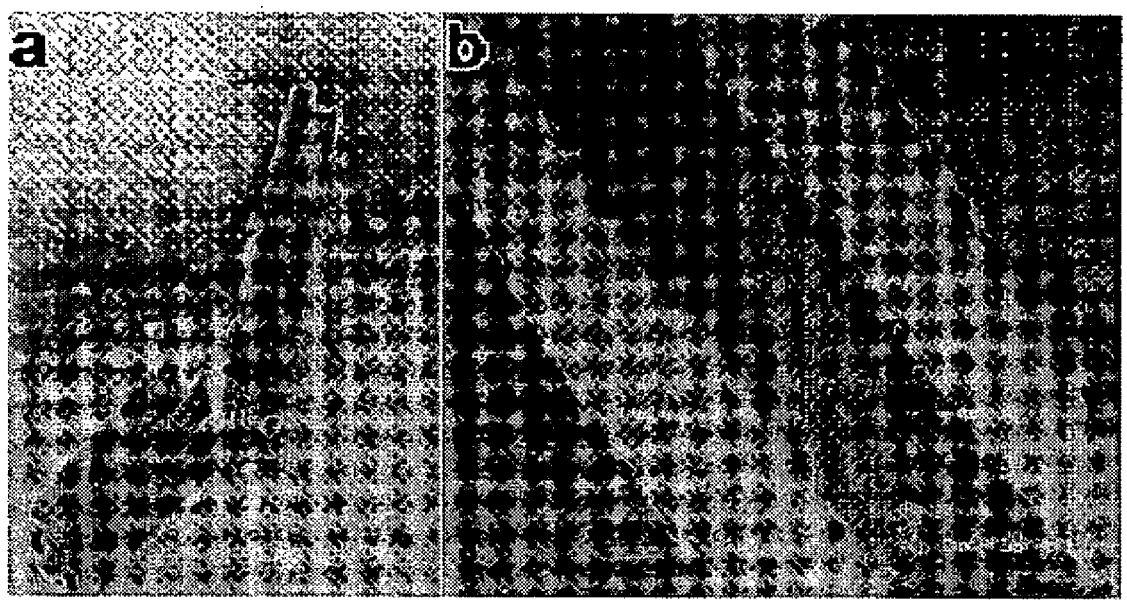
FIG. 3a shows localised expression of GUS activity at the cut site and demonstrates responsiveness of the promoter sequence of SEQ ID NO:2 to mechanical stimulus.
FIG. 3b shows expression of GUS activity in leaves that were subjected to a hydration/dehydration cycle and demonstrates responsiveness of the promoter sequence of SEQ ID NO:2 to dehydration stress.

Dehydration tests were performed on $T_1$, rice plants undergoing active tillering (35 days after sowing). Plants were exposed to a drought period of 15 days, during this time water was withheld. Dehydration stress was monitored during this period and gave rise to the following symptoms: curled leaves, altered leaf colour, loss of leaf turgor and visual loss of chlorophyll. Following this period, plants were rehydrated for 3 days. Leaves were sampled during the hydration/dehydration cycle and stained in GUS staining solution (Jefferson R. A., et al., 1987. EMBO 6:3901-3907) as shown in FIG. 3. GUS staining is shown throughout the leaves, demonstrating responsiveness of the promoter to dehydration stimulus.

Figure 5:
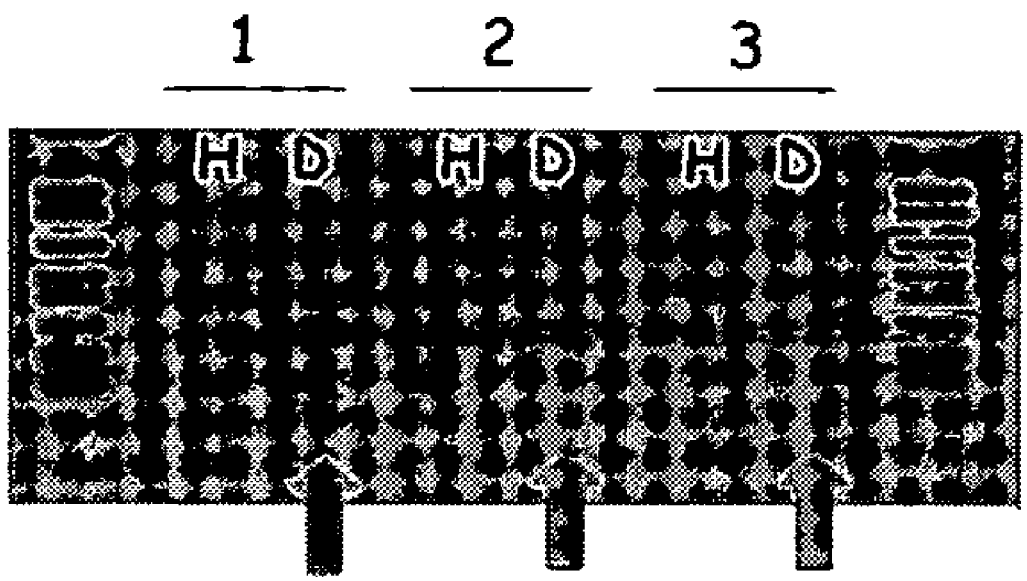
FIG. 5 shows induction of expression of the vacuolar pyrophosphatase transcript, fused to the promoter in transgenic ryegrass, in response to dehydration and demonstrates the responsiveness of the promoter sequence of SEQ ID NO:1 to dehydration stress. Numbers 1, 2, and 3 represent three different transgenic lines. H means hydrated and D means dehydrated.

Dehydration tests were also performed on $T_0$ perennial ryegrass plants transformed with the promoter/vacuolar pyrophosphatase construct described above, 35 days after transplanting to glasshouse. Plants were well-watered before sampling. Leaves were then sampled by harvesting the leaf and allowing the cut leaves to wilt on the bench in the greenhouse for a minimum of 30 minutes. Fresh-cut hydrated (H) and wilting dehydrated (D) leaves from the three $T_0$ perennial ryegrass leaves were ground to a powder, separately, in liquid nitrogen and total RNA isolated using a commercial plant RNA isolation kit (RNeasy Plant Mini Kit, Qiagen, CA, USA). Using 5 μg of total RNA from each sample, first strand cDNA were synthesised using SuperScript™ III Reverse Transcriptase (Invitrogen, CA., USA). Using aliquots of the first strand cDNA from fresh-cut hydrated and wilted $T_0$ transgenic perennial ryegrass leaf, RT-PCR was performed using oligonucleotide primer sequences (SEQ ID NO:19-20) to detect the presence of the vacuolar pyrophosphatase transcript (VP) (FIG. 5). FIG. 5 shows that the expression of VP is enhanced when the leaves are wilted and demonstrates the responsiveness of the promoter (driving expression of VP) to dehydration stress.

The above Examples illustrate practice of the invention. It will be appreciated by those skilled in the art that numerous variations and modifications may be made without departing from the spirit and scope of the invention.

The invention claimed is:

1. An isolated stress-responsive promoter polynucleotide, comprising:
   a) the sequence of SEQ ID NO:1
   b) a sequence with at least 98% identity to the sequence of SEQ ID NO:1; or
   c) the sequence of SEQ ID NO: 2.

2. A genetic construct comprising the promoter polynucleotide of claim 1.

3. The genetic construct of claim 2, wherein the promoter polynucleotide is operably linked to a polynucleotide sequence of interest.

4. The genetic construct of claim 3, wherein the polynucleotide sequence of interest encodes a stress-protective polypeptide.

5. The genetic construct of claim 4, wherein the stress-protective polypeptide is a vacuolar pyrophosphatase.

6. The genetic construct of claim 5, wherein the vacuolar pyrophosphatase comprises the sequence of SEQ ID NO:4.

7. The genetic construct of claim 6, wherein the polynucleotide sequence encoding said vacuolar pyrophosphatase comprises the coding sequence of SEQ ID NO:5.

8. The genetic construct of claim 6, wherein the polynucleotide sequence encoding said vacuolar pyrophosphatase comprises the coding sequence of SEQ ID NO:6.

9. A vector comprising the genetic construct of claim 2.

10. A host cell transformed with the promoter polynucleotide of claim 1.

11. A plant cell transformed with the promoter polynucleotide of claim 1.

12. A plant cell transformed with the genetic construct of claim 2.

13. A plant comprising the plant cell of claim 11.

14. A plant comprising the plant cell of claim 12.

15. A method for producing a plant cell or plant with modified expression of at least one polynucleotide sequence of interest, the method comprising the step of transforming a plant cell or plant with the genetic construct of claim 3.

16. A plant produced by the method of claim 15.

17. A seed, propagule, progeny or part of the plant of claim 13, wherein the seed, propagule, progeny or part of the plant comprises the promoter polynucleotide.

18. A seed, propagule, progeny or part of the plant of claim 14, wherein the seed, propagule, progeny or part of the plant comprises the genetic construct.

19. A seed, propagule, progeny or part of the plant of claim 16, wherein the seed, propagule, progeny or part of the plant comprises the genetic construct.

* * * * *

UNITED STATES PATENT AND TRADEMARK OFFICE
CERTIFICATE OF CORRECTION

| | | |
|---|---|---|
| PATENT NO. | : 7,659,449 B2 | Page 1 of 1 |
| APPLICATION NO. | : 11/501283 | |
| DATED | : February 9, 2010 | |
| INVENTOR(S) | : Smith-Espinoza et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 101 days.

Signed and Sealed this

Twenty-eighth Day of December, 2010

David J. Kappos
*Director of the United States Patent and Trademark Office*